United States Patent [19]

Clark et al.

[11] Patent Number: 5,229,387
[45] Date of Patent: Jul. 20, 1993

[54] DECAHYDRO-8H-ISOQUINO[2,1-G][1,6]NAPHTHYRIDINE AND DECAHYDROBENZO[A]PYRROLO[2,3-E]QUINOLIZINE DERIVATIVES

[75] Inventors: Robin D. Clark, Palo Alto; Brian H. Vickery, Mountain View, both of Calif.; Mike Spedding, Edinburgh, Scotland

[73] Assignee: Syntex (U.S.A.) Inc., Palo Alto, Calif.

[21] Appl. No.: 763,469

[22] Filed: Sep. 20, 1991

[51] Int. Cl.$^5$ .................... C07D 455/03; A61K 31/47
[52] U.S. Cl. ..................... 514/253; 514/280; 514/285; 544/361; 546/16; 546/48; 546/70; 546/79; 546/101; 546/139; 548/531; 548/536
[58] Field of Search ............ 546/16, 50, 51, 70, 546/48; 544/361; 514/253, 280, 283, 285

[56] References Cited

U.S. PATENT DOCUMENTS

| | | | |
|---|---|---|---|
| 4,454,139 | 6/1984 | Ward et al. | 424/258 |
| 4,550,114 | 2/1985 | White | 514/294 |
| 4,791,108 | 7/1988 | Clark | 514/233.2 |
| 4,886,798 | 12/1989 | Clark | 514/233.2 |
| 4,956,365 | 9/1990 | Clark et al. | 514/233.2 |
| 5,013,761 | 5/1991 | Beedle et al. | 514/650 |
| 5,134,140 | 7/1992 | Stack | 546/16 |

FOREIGN PATENT DOCUMENTS

0259092A1 2/1987 European Pat. Off.

OTHER PUBLICATIONS

Clark et al., *J. Med. Chem.* 34, pp. 705-711 (1991).
Investigation on the Chemistry of Berbans, by Szabo et al., *Nouv. J. Chimie*, 4(3), 199-202 (1980).

*Primary Examiner*—Donald G. Daus
*Assistant Examiner*—E. Bernhardt
*Attorney, Agent, or Firm*—Brian Lewis; David A. Lowin; Tom M. Moran

[57] ABSTRACT

Compounds of the formula

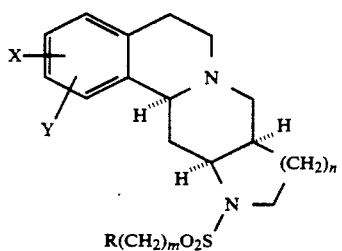

(I)

wherein:

m is an integer of 1-6;
n is an integer of 1 or 2;
X and Y are independently hydrogen; hydroxy; lower alkyl; lower alkoxy; or halo; or X and Y when adjacent and taken together are methylenedioxy or ethylene-1,2-dioxy;
R is

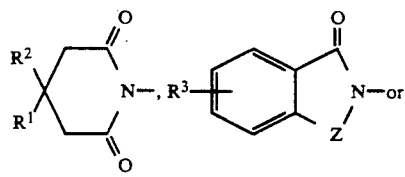

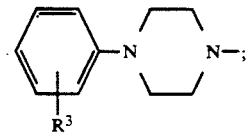

wherein:
$R^1$ and $R^2$ are independently hydrogen or lower alkyl, or when taken together with the carbon to which they are attached are cycloalkyl;
$R^3$ is hydrogen, lower alkyl, lower alkoxy, hydroxy, trifluoromethyl or halo; and

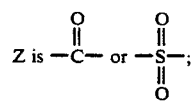

and pharmaceutically acceptable acid addition salts thereof. The compounds and salts exhibit useful pharmacological properties, including selective $\alpha_2$-adrenoceptor antagonist properties and 5-HT$_{1A}$ receptor partial agonist properties, and are particularly useful for the treatment of sexual dysfunction, depression and anxiety.

28 Claims, No Drawings

DECAHYDRO-8H-ISOQUINO[2,1-G][1,6]NAPH-THYRIDINE AND DECAHYDROBENZO[A]PYRROLO[2,3-E]QUINOLIZINE DERIVATIVES

BACKGROUND OF THE INVENTION

1. Field of the Invention

This invention relates to various decahydro-8H-isoquino[2,1-g][1,6]-naphthyridine and decahydrobenzo[a]pyrrolo[2,3-e]quinolizine derivatives, the compounds of formula (I), and pharmaceutically acceptable salts thereof, which exhibit useful pharmacological properties, including selective $\alpha_2$-adrenoceptor antagonist properties and 5-HT$_{1A}$ receptor partial agonist properties.

Selective $\alpha_2$-adrenoceptor antagonists are known to block the effects of adrenaline and noradrenaline on the noradrenergic system in mammals, causing many different results, including increased noradrenaline release from noradrenergic nerve endings. Such a result has been found to be beneficial in the treatment of disease states such as depression, impotence, sexual dysfunction, and for a variety of vascular disorders (see, for example, McGrath, Brown and Wilson, Med. Res. Rev., Vol. 9, pp. 407-533 (1989)).

Partial agonists of 5-HT$_{1A}$ (5-hydroxytryptamine) receptors modify serotonergic function in mammals, and have been found to be useful in the treatment of disorders such as anxiety, depression, sexual dysfunction, impotence and eating disorders (see, for example, New, Med. Res. Rev., Vol. 10, pp 283-326 (1990)).

The compounds of formula (I) are thus useful for the treatment of various disease states, including those disease states alleviable by treatment with compounds having selective $\alpha_2$-adrenoceptor antagonist activity and/or 5-HT$_{1A}$ receptor partial agonist activity in mammals. Such treatment includes, for example, lowering of blood pressure in normotensive and hypertensive mammals, treatment of disorders of peripheral blood flow, wound healing, inhibition of platelet aggregation, treatment of sexual dysfunction, alleviation of depression, treatment of anxiety, alleviation of male impotence, lowering of intraocular pressure, and palliation of diabetes and its sequelae such as diabetic retinopathy, nephropathy, neuropathy and associated circulatory disturbances. The compounds of formula (I) are particularly useful for the treatment of sexual dysfunction, depression and anxiety.

2. Previous Disclosures

The novel compounds of this invention are various decahydro-8H-isoquino[2,1-g][1,6]naphthyridine and decahydrobenzo[a]pyrrolo[2,3-e]quinolizine derivatives, the compounds of formula (I). Compounds somewhat structurally related are described in U.S. Pat. Nos. 4,454,139, 4,550,114, 4,791,108, 4,886,798, and in Nouveau J. Chim. 4(3), 199-202 (1980).

SUMMARY OF THE INVENTION

One aspect of the invention concerns novel compounds, as single enantiomers or racemic mixtures, represented by the formula:

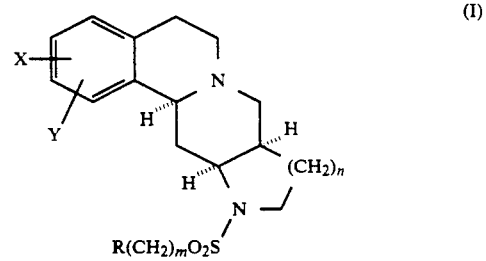

wherein:
m is an integer of 1-6;
n is an integer of 1 or 2;
X and Y are independently hydrogen; hydroxy; lower alkyl; lower alkoxy; or halo; or X and Y when adjacent and taken together are methylenedioxy or ethylene-1,2-dioxy;
R is

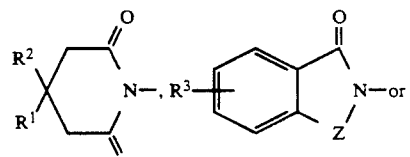

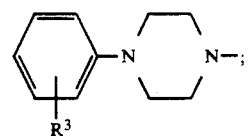

wherein:
R$^1$ and R$^2$ are independently hydrogen or lower alkyl, or when taken together with the carbon to which they are attached are cycloalkyl;
R$^3$ is hydrogen, lower alkyl, lower alkoxy, hydroxy, trifluoromethyl or halo; and

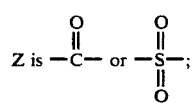

and pharmaceutically acceptable acid addition salts thereof, active for example as selective $\alpha_2$-adrenoceptor antagonists and/or 5-HT$_{1A}$ receptor partial agonists in mammals.

In another aspect, the invention relates to pharmaceutical compositions containing a therapeutically effective amount of a compound of Formula (I), or a pharmaceutically acceptable salt thereof, in admixture with one or more pharmaceutically acceptable, non-toxic carriers.

In yet another aspect, the invention relates to a method for treating a mammal having a disease state which is alleviable by treatment with a compound of formula (I), acting for example as a selective $\alpha_2$-adrenoceptor antagonist and/or a 5-HT$_{1A}$ receptor partial agonist, especially where the disease state is sexual dysfunction, depression or anxiety, by administering to a mammal in need thereof a therapeutically effective amount of a compound of Formula (I), or a pharmaceutically acceptable salt thereof.

DETAILED DESCRIPTION OF THE INVENTION

Definitions

As used herein:

"Alkyl" means a branched or unbranched saturated hydrocarbon chain containing 1 to 8 carbon atoms, such as methyl, ethyl, propyl, tert-butyl, n-hexyl, n-octyl and the like.

"Lower alkyl" means a branched or unbranched saturated hydrocarbon chain containing 1 to 6 carbon atoms, such as methyl, ethyl, propyl, isopropyl, tert-butyl, butyl, n-hexyl and the like, unless otherwise indicated.

"Lower alkoxy" means the group -O-(lower alkyl) wherein lower alkyl is as herein defined.

"Cycloalkyl" means a saturated monovalent monocyclic hydrocarbon radical containing 3-8 carbon atoms, such as cyclopropyl, cyclobutyl, cyclopentyl, cyclohexyl, cycloheptyl and cyclooctyl.

"Halo" denotes fluoro, chloro, bromo, or iodo, unless otherwise indicated.

The terms "inert organic solvent" or "inert solvent" mean a solvent inert under the conditions of the reaction being described in conjunction therewith [including, for example, benzene, toluene, acetonitrile, tetrahydrofuran ("THF"), dimethylformamide ("DMF"), chloroform ("CHCl$_3$"), methylene chloride (or dichloromethane or "CH$_2$Cl$_2$"), diethyl ether, ethyl acetate, acetone, methylethyl ketone, methanol, ethanol, propanol, isopropanol, tert-butanol, dioxane, pyridine, and the like]. Unless specified to the contrary, the solvents used in the reactions of the present invention are inert solvents.

"Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

"Optional" or "optionally" means that the subsequently described event or circumstance may or may not occur, and that the description includes instances where said event or circumstance occurs and instances in which it does not. For example, "optionally followed by converting the free base to the acid addition salt" means that said conversion may or may not be carried out in order for the process described to fall within the invention, and the invention includes those processes wherein the free base is converted to the acid addition salt and those processes in which it is not.

The terms "α and β" indicate the specific stereochemical configuration of a substituent at an asymmetric carbon atom in a chemical structure as drawn. Thus "α", denoted by a broken line, indicates that the group at the position in question is below the general plane of the molecule as drawn, and "β", denoted by a bold line, indicates that the group at the position in question is above the general plane of the molecule as drawn.

It should be understood that formula (I) as drawn is intended to represent the racemic form of compounds of formula (I) as well as the individual enantiomers and non-racemic mixtures thereof, although for the sake of clarity only one enantiomer is shown. For the purpose of illustration the two enantiomers of compounds of formula (I) are represented below as (IA) and (IB):

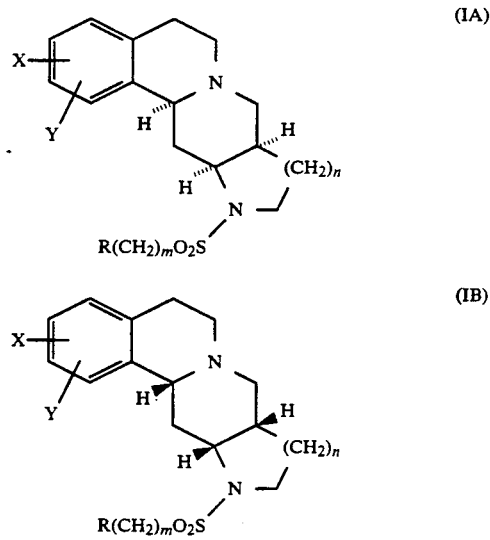

The scope of the invention as described and claimed encompasses the racemic forms of the compounds of formula (I) as well as the individual enantiomers of formula (IA) and (IB), and non-racemic mixtures thereof.

The symbol "(±)" is used to designate a racemic mixture of individual (+) and (−) isomers. When the compound of formula (I) is a pure enantiomer, the stereochemistry at each chiral carbon atom is specified by either R or S according to the Cahn-Ingold-Prelog R-S system. In this manner relative stereochemistry is conveyed unambiguously.

"Isomers" are different compounds that have the same molecular formula.

"Stereoisomers" are isomers that differ only in the way the atoms are arranged in space.

"Enantiomers" are a pair of stereoisomers that are non-superimposable mirror images of each other. A 1:1 mixture of a pair of enantiomers is a "racemic" mixture.

"Diastereoisomers" are stereoisomers which are not mirror-images of each other.

The term "treatment" as used herein covers any treatment of a disease in a mammal, particularly a human, and includes:

(i) preventing the disease from occurring in a subject which may be predisposed to the disease but has not yet been diagnosed as having it;

(ii) inhibiting the disease, i.e., arresting its development; or (iii) relieving the disease, i.e., causing regression of the disease.

The term "disease state which is alleviable by treatment with an β$_2$-adrenoceptor antagonist or a 5-HT$_{1A}$ receptor partial agonist" as used herein is intended to cover all disease states which are generally acknowledged in the art to be usefully treated with either α$_2$-adrenoceptor antagonists or 5-HT$_{1A}$ receptor partial agonists in general, or disease states usefully treated by compounds combining both such activities, and those disease states which have been found to be usefully treated by the specific compounds of our invention, the compounds of formula (I). Such disease states include, but are not limited to, depression, anxiety, elevated blood pressure in hypertensive mammals, platelet aggregation, male impotence, elevated intraocular pressure, disorders of peripheral blood flow, wound healing, and diabetes and its sequelae such as diabetic retinopathy, nephropathy, neuropathy and associated circulatory disturbances.

The compounds of the invention include those compounds where n is 1 and those where n is 2. The compounds of formula (I) where n is 2, illustrated below, will be named using the indicated numbering system:

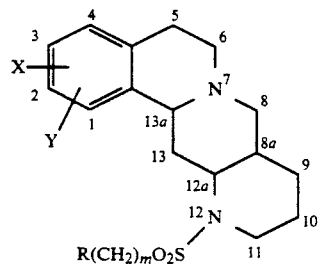

Following are examples of how representative compounds of formula (I) where n is 2 are named:

A racemic compound of formula (I) wherein X is 3-methoxy, Y is hydrogen, m is 3, and R is

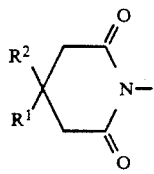

where $R^1$ and $R^2$ taken together with the carbon to which they are attached are cyclopentyl, is named:
(±)-(8aα,12aα,13aα)-3-methoxy-12-[8-(3-propyl)-8-azaspiro [4.5]decan-7,9-dione]sulfonyl-5,6,8a,9,10,11,12,12a,-13,13a-decahydro-8H-isoquino[2,1-g][1,6-naphthyridine.

The (+) -isomer of a compound of formula (I) wherein X and Y taken together are 2,3-methylenedixoy, m is 2 and R is 4-phenylpiperazin-1-yl is named:
(8aR, 12aS, 13aS)-2,3-methylenedioxy-12-[2-(4-phenylpiperazin-1yl)ethanesulfonyl]-5,6,8a9,10,11, 12,12a,13, 13a-decahydro-8H-isoquino[2,1-g][1,6]-naphthyridine.

The compounds of formula (I) where n is 1, illustrated below, will be named using the indicated numbering system:

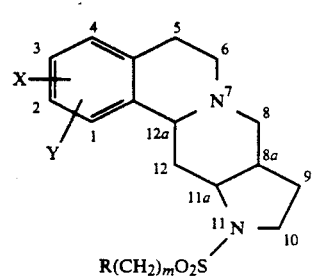

Following are examples of how representative compounds of formula (I) where n is 1 are named:

A racemic compound of formula (I) wherein X is 3-methoxy, Y is hydrogen, m is 3 and R is

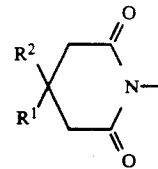

where $R^1$ and $R^2$ taken together with the carbon to which they are attached are cyclopentyl, is named:
(3S)-(8a,α,11aα,12aα) -3-methoxy-11-[8-(3-propyl)-8-azaspiro[4.5]decan-7,9-dione]sulfonyl-5,6,8,8a,9,10,11,-11a,12,12a-decahydrobenzo]a]pyrrolo[2,3-e]quinolizine.

The (±)-isomer of a compound of formula (I) wherein X and Y taken together are 2,3-methylenedioxy, m is 4 and R is

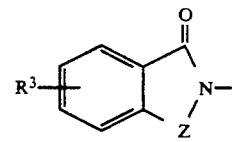

where $R^3$ is hydrogen and Z is $-SO_2$, is named:
(8aR,11aS,12aS)-2,3-methylenedioxy-11-{4-[2-(benzoisothiazole-3(2H)-one-1,1-dioxide)]butanesulfonyl}-5,6,8,8a,9,10,11,11a,12,12a-decahydrobenzo[a]pyrrolo[2,3-e]quinolizine.

PREFERRED EMBODIMENTS

Among the family of compounds of the present invention, a preferred group includes the compounds in which n is 2. Within this group a preferred subgroup includes the compounds wherein R is:

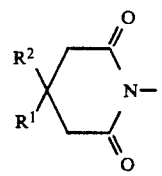

One preferred class within this subgroup includes compounds in which X and Y are independently hydrogen or lower alkoxy, or X and Y taken together is methylenedioxy, in particular where m is 3. Within this class a preferred subclass is that where X is 3-methoxy and Y is hydrogen, and $R^1$ and $R^2$ are both methyl or $R^1$ and $R^2$ together with the carbon atom to which they are attached are cyclopentyl, most preferably as the (±) isomer.

A second preferred subgroup includes the compounds wherein R is:

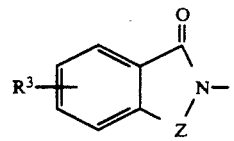

One preferred class within this subgroup includes compounds in which X and y are independently hydrogen or lower alkoxy, or X and Y taken together is methylenedioxy, in particular where m is 3 and Z is —SO₂.

A third preferred subgroup includes the compounds wherein R is:

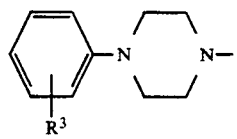

One preferred class within this subgroup includes compounds in which X and Y are independently hydrogen or lower alkoxy, or X and Y taken together is methylenedioxy, in particular where m is 3 and R³ is lower alkoxy.

a second preferred group includes the compounds in which n is 1. Within this group a preferred subgroup includes the compounds wherein R is:

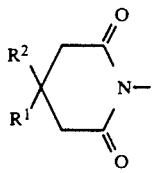

One preferred class within this subgroup includes compounds in which X and y are independently hydrogen or lower alkoxy, or X and Y taken together is methylenedioxy.

A second preferred subgroup includes the compounds where R is:

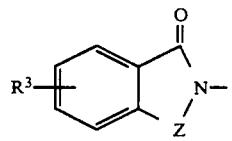

One preferred class within this subgroup includes compounds in which X and Y are independently hydrogen or lower alkoxy, or X and Y taken together is methylenedioxy.

A third preferred subgroup includes the compounds where R is:

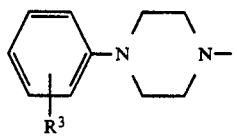

One preferred class within this subgroup includes compounds in which X and Y are independently hydrogen or lower alkoxy, or X and y taken together is methylenedioxy.

At present, the preferred compounds are:
(8aR,12aS,13aS)-3-methoxy-12-[8-(3-propyl)-8-azaspiro[4.5]decan-7,9-dione]sulfonyl-5,6,8a,9,10,11,12,-12a,13, 13a-decahydro-8H-isoquino[2,1-g][1,6]naphthyridine; and
(8aR, 12a,S, 13aS)-3-methoxy-12-[3-(3,3-dimethylglutarimid-1-yl)propanesulfonyl]-5,6,8a,9,10,11,12,-12a,13,13a-decahydro-8H-isoquino[2,1-g][1,6]naphthyridine.

METHODS OF PREPARATION

Preparation of Compounds of Formula (VII)

The racemic compounds of formula (I) where n is 2 are prepared from the intermediates of formula (VII), the preparation of which is illustrated below in Reaction Scheme I.

It should be understood that the structures unless otherwise indicated in the text are intended to represent racemic mixtures, although for the sake of clarity only one enantiomer is shown.

REACTION SCHEME I

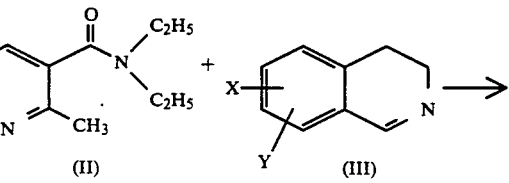

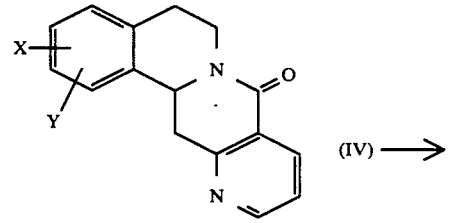

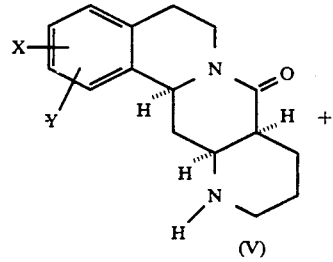

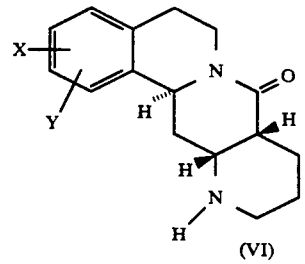

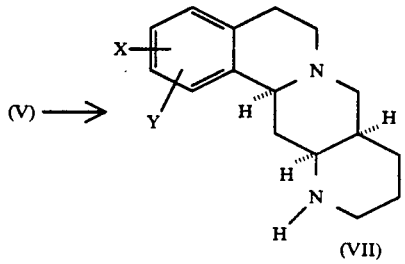

Preparation of Compounds of Formula (IV)

The intermediate of formula (II), 2-methylnicotinic acid diethylamide, is prepared according to the method disclosed in Ber., 72B, 563 (1939). The intermediates of formula (III), optionally substituted dihydroisoquinolines, are prepared according to the method of Bischler-Napieralski, disclosed in *Organic Reactions*, Vol. VI, p 74 (1951), by the cyclization of formamides of commercially available optionally substituted phenylethylamines. To prepare the compounds of formula (IV), the compounds of formula (II) and (III) are reacted together in the presence of a strong base (for example, potassium t-butoxide, sodamide, sodium triphenylmethane, lithium diethylamide or lithium diisopropylamide, preferably lithium diisopropylamide). The reaction is preferably carried out in an ethereal solvent (for example diethyl ether, dimethoxyethane, dioxane or tetrahydrofuran, preferably tetrahydrofuran), at a temperature of about 0° C. to −50° C., preferably at about −10° C. to −40° C., for about 30 minutes to 4 hours. For example, diisopropylamine is dissolved in an ethereal solvent, preferably tetrahydrofuran, and cooled to a temperature of about −20° to −80° C., preferably about −65° C. To the cooled solution about 1 molar equivalent of an alkyl lithium, preferably 1.6M n-butyllithium, is added. To this cold solution is added a mixture of about 1 molar equivalent of the compound of formula (II) and about 1 molar equivalent of the compound of formula (III) in an ethereal solvent, preferably tetrahydrofuran. The reaction mixture is allowed to warm to about −10° to −40° C., preferably about −20° C., over a period of about 1 hour, and the reaction then quenched with an acid, preferably hydrochloric acid. The product of formula (IV), a (±)-5,6,13,13a-tetrahydroisoquino[2,1-g][1,6]naphthyridine-8-one hydrochloride, is isolated and purified by conventional means, preferably recrystallization of an acid salt.

Preparation of Compounds of Formula (V) and (VI)

A compound of formula (IV) as an acid salt, preferably the hydrochloride, is then hydrogenated in an inert solvent with a suitable heterogeneous catalyst, for example palladium on carbon, platinum oxide or preferably rhodium on alumina, to give the corresponding mixture of diastereoisomers of formula (V) and (VI). For example, for every gram of the hydrochloride of the compound of formula (IV) in a solution of acetic acid is added from 0.1 to 0.6 g, preferably about 0.25 g, of 5% rhodium on alumina catalyst and the mixture hydrogenated at a pressure of about 25-80 psi, preferably about 50 psi. The reaction is conducted at a temperature of about 0° to 50° C., preferably about 25° C., for about 24 to 72 hours, preferably about 42 hours. When the reaction is substantially complete, the mixture of compounds of formula (IV) and (V) is isolated by conventional means and the mixture chromatography on silica gel, eluting with a suitable solvent mixture, for example 5-20% methanol in methylene chloride. The first component eluted is a (±)-5,6,8aβ, 9,10,11,12,12aβ,13,13aα-decahydroisoquino[2,1-g][1,6]naphthyridine-8-one derivative, a compound of formula (VI), and the second component eluted is a (±)-5,6,8aα,9,10,11,12,12aα,13,13a -decahydroisoquino[2,1-q][1,6]naphthyridin-8-one derivative, a compound of formula (V).

Preparation of Compounds of Formula (VII)

A compound of formula (V) is then reduced to the corresponding compound of formula (VII) with a suitable reducing agent (for example borane, triethyloxonium fluoroborate followed by sodium borohydride, sodium borohydride in the presence of a carboxylic acid, or lithium aluminum hydride, preferably lithium aluminum hydride) For example, a solution of a compound of formula (V) in an ethereal solvent, preferably tetrahydrofuran, is slowly added to a solution of about 1 to 4 molar equivalents, preferably about 1.5 to 2 molar equivalents, of lithium aluminum hydride in the same ethereal solvent at about 25° C. The mixture is then refluxed for about 1-10 hours, preferably about 3 hours. When the reaction is substantially complete, the (±)-5,6,8aα,9,10,11,12,12aα,13,13aα-decahydro-8H-isoquino[2,1-g][1,6]naphthyridine derivative, a compound of formula (VII), is separated and purified by conventional means, for example recrystallization of an acid salt.

Separation of Optical Isomers of (V), (VI) or (VII)

Methods of obtaining the optical isomers of the compounds of formulae (V), (VI) and (VII) and related compounds is disclosed in U.S. Pat. No. 4,886,798, the complete disclosure of which is hereby incorporated by reference. For example, a racemic compound of formula (V) is separable into two enantiomers, which are represented below as compounds of formulae (VA) and (VB):

(VA)

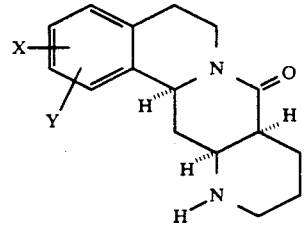

(VB)

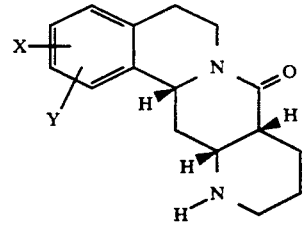

A preferred procedure for the preparation of the enantiomers of formula (VA) is set forth in a copending U.S. application, Ser. No. 07/673,693, the complete disclosure of which is hereby incorporated by reference. The subject matter and the claimed invention of both the present application and the above application are subject to an obligation of assignment to the same Research Organization.

An enantiomer of formulae (VA) or (VB) is then reduced (in the same manner as shown above for the reduction of racemic (V)) to the appropriate enantiomer of a compound of formula (VII), which are illustrated below as (VIIA) and (VIIB).

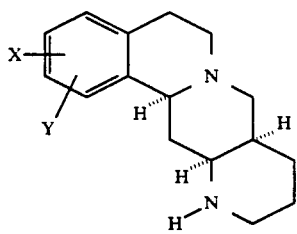
(VIIA)

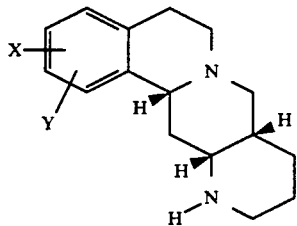
(VIIB)

Preparation of Compounds of Formula (XI)

The compounds of formula (I) where n is 1 are prepared from the intermediates of formula (XI), the preparation of which is illustrated below in Reaction Scheme II.

It should be understood that the structures unless otherwise indicated are intended to represent racemic mixtures, although for the sake of clarity only one enantiomer is shown.

REACTION SCHEME II

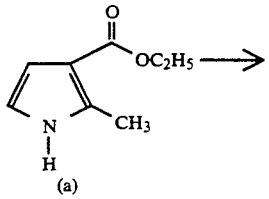
(VIII)

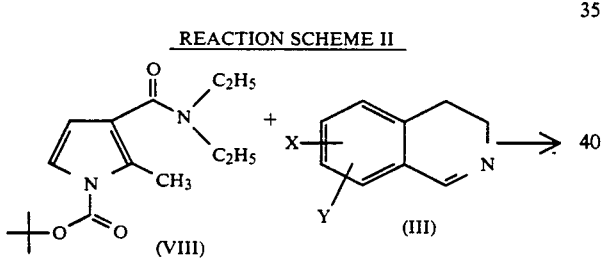 (III)

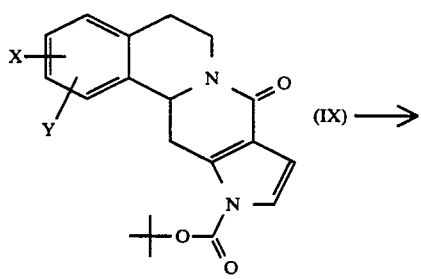 (IX) →

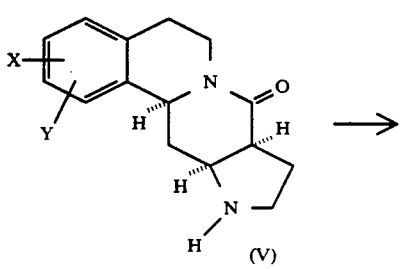 (V)

-continued
REACTION SCHEME II

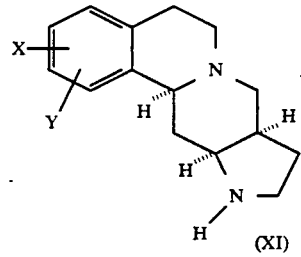
(XI)

Preparation of the Intermediate of Formula (VIII)

The intermediate of formula (VIII), 1-tert-butoxycarbonyl-2-methylpyrrole-3-carboxylic acid diethylamide, is prepared from 3-(ethoxycarbonyl)-2-methylpyrrole, as shown in Reaction Scheme III below:

REACTION SCHEME III

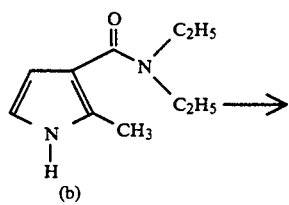
(a)

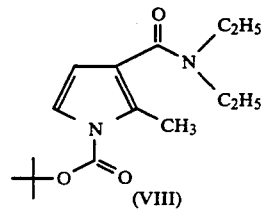
(b)

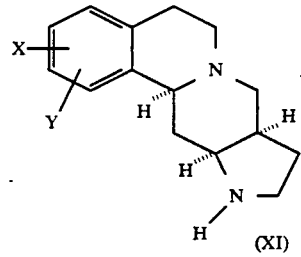
(VIII)

The starting 3-(ethoxycarbonyl)-2-methylpyrrole of formula (a) is prepared by the method disclosed in J. Org. Chem., Vol. 49, pp 3327–3336 (1984). This material is converted to 2-methylpyrrole-3-carboxylic acid diethylamide of formula (b), according to the method disclosed in Tetrahedron Letters, No. 48, pp 4171–4174 (1977), which is converted to 1-tert-butoxycarbonyl-2-methylpyrrole-3-carboxylic acid diethylamide of formula (VIII) by the procedure disclosed in J. Org. Chem., Vol. 46, pp 157–164 (1981).

Preparation of Compounds of Formula (IX)

To prepare a compound of formula (IX), the anion of a compound of formula (VIII) is first formed by reaction with a strong base (for example potassium t-butoxide, sodamide, sodium triphenylmethane, lithium diethylamide, or lithium diisopropylamide, preferably lithium diisopropylamide). The reaction is preferably carried out in an ethereal solvent (for example diethyl ether, dimethoxyethane, dioxane, or tetrahydrofuran, most preferably tetrahydrofuran), at a temperature of about −100° C. to −50° C., preferably at about −70° C., for about 5 minutes to 1 hour, preferably about 30 minutes. For example, diisopropylamine is dissolved in an ethereal solvent, preferably tetrahydrofuran, and cooled to a temperature of about −60° to −80° C., preferably about −70° C. To the cooled solution about 1 molar equivalent of an alkyl lithium, preferably 6M n-butyllithium, is added. To this cold solution is added a mixture of about 1 molar equivalent of a compound of formula (VIII) in an ethereal solvent, preferably tetrahydrofuran, followed by about 1 molar equivalent of a compound of formula (III) in the same solvent. After about 5 minutes to 1 hour, preferably about 30 minutes, the reaction mixture is allowed to warm to about −20° to −40° C., preferably about −30° C., over a period of about 30 minutes, and quenched with water. The (±)-11-(tert-butoxycarbonyl)benzo[a]pyrrole[2,3-e]quinolizin-8-one derivative, a compound of formula (IX), is isolated and purified by conventional means, preferably chromatography followed by recrystallization.

Preparation of Compounds of Formula (X)

A compound of formula (IX) is then hydrogenated with a suitable heterogeneous catalyst, for example palladium on carbon, platinum oxide or preferably rhodium on alumina, to give the corresponding compound of formula (X). For example, for every gram of a compound of formula (IX) dissolved in a suitable solvent, for example acetic acid or preferably ethanol, is added from 0.1 to 0.6 g, preferably about 0.25 g, of 5% rhodium on alumina catalyst and the mixture hydrogenated at a pressure of about 25–80 psi, preferably about 40 psi. The reaction is conducted at a temperature of about 0° to 50° C., preferably about 25° C., until uptake of hydrogen ceases, usually about 2–4 hours. When the reaction is substantially complete, the product is separated conventionally and dissolved in an inert organic solvent, preferably dichloromethane. An excess of a strong acid, preferably trifluoroacetic acid, is then added in order to remove the t-butoxycarbonyl protecting group. The reaction is conducted at a temperature of about 0° to 50° C., preferably about 25° C., for about 5–48 hours, preferably about 18 hours. When the reaction is complete a (±)-(8aα,11aα,12aα)-5,6,8,8a,9,10,11,11a,12,12a-decayhydrobenzo]2,3-e]quinolizin-8-one derivative, a compound of formula (X), is separated and purified by conventional means, preferably chromatography on silica gel.

Preparation of Compounds of Formula (XI)

A compound of formula (X) is then reduced to a compound of formula (XI) with a suitable reducing agent (for example borane, triethyloxonium fluoroborate followed by sodium borohydride, sodium borohydride in the presence of a carboxylic acid, or lithium aluminum hydride, preferably lithium aluminum hydride). For example, a solution of a compound of formula (X) in an ethereal solvent, preferably tetrahydrofuran, is slowly added to a solution of about 1 to 4 molar equivalents, preferably about 1.5 to 2 molar equivalents, of lithium aluminum hydride in the same ethereal solvent at about 25° C. The mixture is then refluxed for about 1–10 hours, preferably about 3 hours. When the reaction is substantially complete, a (±)-(8aα,11aα,12aα)-5,6,8,8a,9,10,11,11a,12,12a-decahydrobenzo[a]pyrrolo[2,3-e]quinolizine derivative, a compound of formula (XI), is separated and purified by conventional means, or alternatively may be used in the next reaction with no further purification.

Separation of Optical Isomers of (X) or (XI)

The optical isomers of the compounds of formula (X) or (XI) may be obtained by conventional resolution means; for example by separation (e.g. fractional crystallization) of the diastereomeric salts formed by the reaction of a compound of formula (X) or (XI) with an optically active acid, at temperatures between 0° C. and the reflux temperature of the solvent employed for fractional crystallization. Exemplary of such optically active acids are the optically active forms of camphor-10-sulfonic acid, 2-bromo-camphor-10-sulfonic acid, camphoric acid, menthoxyacetic acid, tartaric acid, malic acid, diacetyltartaric acid, pyrrolidine-5-carboxylic acid and the like. The separated pure diastereomeric salts may then be cleaved by standard means, such as treatment with a base, to afford the respective optical isomers of the compounds of formula (X) or (XI).

Alternatively, similar methods to those discussed above for the preparation of the optical isomers of the compounds of formula (VII) and related compounds may be employed.

Preparation of Compounds of Formula (I)

The compounds of formula (I) are prepared as depicted in Reaction Scheme IV below.

REACTION SCHEME IV

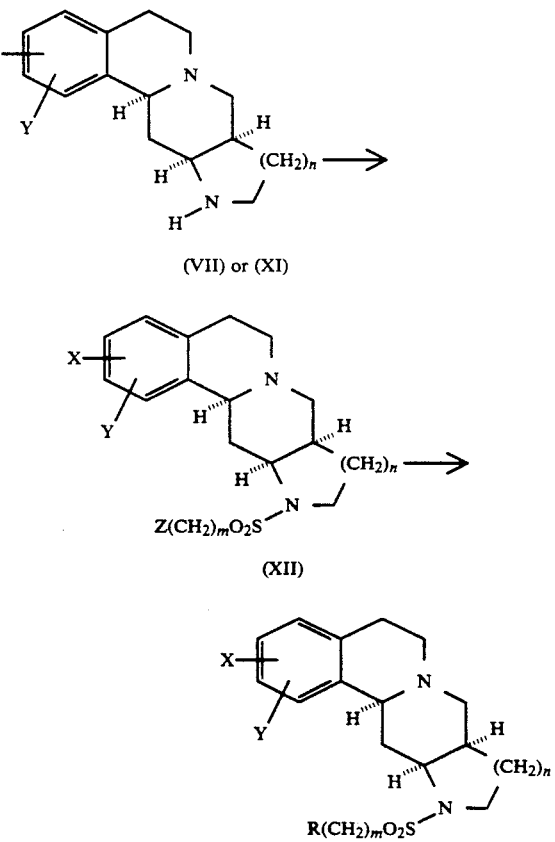

where Z is chlorine or bromine and R, X, Y, n and m are as defined above.

Preparation of Compounds of Formula (XII)

In the first step, a compound of formula (VII) or (XI) is reacted wtih a compound of the formula $Z(CH_2)_mSO_2Z$, where m and Z are as defined above. Compounds of the formula $Z(CH_2)_mSO_2Z$ are commercially available, or may be prepared by procedures well known in the art. The reaction is carried out in an inert organic solvent as defined above, preferably dichloromethane, in the presence of about 1–10 molar equivalents, preferably about 2 molar equivalents, of a base (an inorganic base such as sodium carbonate, potassium bicarbonate or the like, or preferably a tertiary organic base, such as pyridine, N-methylpiperidine, triethylamine, and the like, preferably triethylamine). The mixture is cooled to a temperature of about $-10°$ C. to $30°$ C., preferably about $0°$ C., and about 1–4 molar equivalents, preferably about 1.1 molar equivalents, of the appropriately substituted haloalkylsulfonyl halide of formula $Z(CH_2)_mSO_2Z$ added. The mixture is stirred for about 5 minutes to 1 hour, preferably about 30 minutes. When the reaction is substantially complete the product of formula (XII), an 11-(haloalkanesulfonyl)-5,6,8,8a,9,10,11,11a,12,12a-decahydrobenzo[a]pyrrolo[2,3-e]quinolizine or a 12-(haloalkanesulfonyl)-5,6,8a,9,10,11,12,12a,13,13a-decahydro-8H-isoquino[2,1-g][1,6]naphthyridine, is isolated and purified by conventional means, preferably chromatography followed by recrystallization of an acid salt, preferably a hydrochloride salt.

Preparation of Compounds of Formula (I)

A compound of formula (XII) as the free base is then reacted with a compound of the formula RM, where R is as defined above and M is an alkali metal, preferably sodium. A compound of the formula RM is prepared in situ by first reacting a compound of the formula RH with a metal hydride, preferably sodium hydride. The reaction is carried out in an aprotic polar organic solvent, for example dimethylsulfoxide or preferably N,N-dimethylformamide, at a temperature of about $30°$ C. to $120°$ C., preferably about $80°$ C., for about 30 minutes to 4 hours, preferably about 2 hours. Then about 0.1–1 molar equivalents, preferably about 0.5 molar equivalents, of a compound of formula (XII) is added, together with a catalytic amount of sodium or potassium iodide, and the mixture stirred for about 12 hours to 72 hours, preferably about 16 hours. When the reaction is substantially complete the product of formula (I), an 11-(heterocyclealkanesulfonyl)-5,6,8,8a,9,10,11,11a,12,12a-decahydrobenzo[a]pyrrolo[2,3-e]quinolizine or a 12-(heterocyclealkanesulfonyl)-5,6,8a,9,10,11,12,12a,13,-13a-decahydro-8H-isoquino[2,1-g][1,6]naphthyridine, is isolated and purified by conventional means, preferably chromatography followed by recrystallization of an acid salt, for example a hydrochloride salt.

Preparation of Compounds of Formula (I) where RH is Optionally Substituted 4-Phenyl-1-piperazine In the instance where RH is an optionally substituted 4-phenyl-1-piperazine, the reaction with a compound of formula (XII) may alternatively be carried out by omitting reaction with a metal hydride, and instead carrying out the reaction of about 1–5 molar equivalents, preferably about 2 molar equivalents, of a phenylpiperazine with (XII) directly in the presence of an excess of a base (for example sodium carbonate, potassium bicarbonate or the like, or preferably a tertiary organic base, such as pyridine, N-methylpiperidine, triethylamine, and the like, preferably triethylamine). The reaction is carried out in an aprotic polar organic solvent, for example dimethylsulfoxide or preferably N,N-dimethylformamide, at a temperature of about $50°$ C. to $140°$ C., preferably about $120°$ C., for about 12 hours to 72 hours, preferably about 18 hours. When the reaction is substantially complete the product of formula (I), an optionally substituted 11-[(4-phenyl-1-piperazine)alkanesulfonyl]-5,6,8,8a,9,10,11,11a,12,12a-decahydrobenzo[a]pyrrolo[2,3-e]quinolizine or an optionally substituted 12-[(4-phenyl-1-piperazine)alkanesulfonyl]-5,6,8a,9,10,11,12,12a,13,13a-decahydro-8H-isoquino[2,1-g][1,6]naphthyridine, is isolated and purified by conventional means, preferably chromatography followed by recrystallization of an acid salt, for example a hydrochloride salt.

Isolation and Purification of the Compounds

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be had by reference to the Examples hereinbelow. However, other equivalent separation or isolation procedures could, of course, also be used.

Salts of Compounds of Formula (I)

The compounds of formula (I) may be converted to a corresponding acid addition salt by virtue of the presence of the tertiary nitrogen atoms.

The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained at $0°-50°$ C. The resulting sal precipitates spontaneously or may be brought out of solution with a less polar solvent.

The acid addition salts of the compounds of formula (I) may be converted to the corresponding free bases by treatment with at least a stoichiometric amount of a suitable base such as sodium or potassium hydroxide, potassium carbonate, sodium bicarbonate, ammonia, and the like.

PREFERRED PROCESSES

In summary, the compounds of the present invention are made according to the following last steps.

1. A process for preparing compounds of the formula (I), wherein:

m is an integer of 1–6;

n is 1 or 2;

X and Y are independently hydrogen; hydroxy; lower alkyl; lower alkoxy; or halo; or X and Y when adjacent and taken together are methylenedioxy or ethylene-1,2-dioxy;

R is

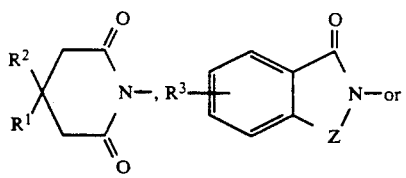

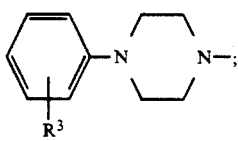

wherein:

$R^1$ and $R^2$ are independently hydrogen or lower alkyl, or when taken together with the carbon to which they are attached are cycloalkyl;

$R^3$ is hydrogen, lower alkyl, lower alkoxy, hydroxy, trifluoromethyl or halo; and

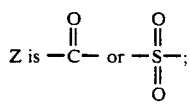

comprises:

(a) reacting a compound of the formula:

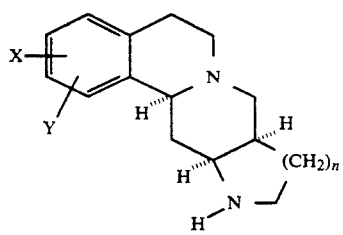

(VII) or (XI)

in which X, Y and n are as defined above, with a compound of the formula $R(CH_2)_mSO_2Z$, where R is as defined above and Z is chlorine or bromine; or (b) reacting the free base of the compound of formula (I) with an acid to give a pharmaceutically acceptable acid addition salt; or (c) reacting an acid addition salt of the compound of formula (I) with a base to give the corresponding free base; or (d) converting an acid addition salt of the compound of formula (i) to another pharmaceutically acceptable acid addition salt of formula (I).

2. Alternatively, a process for preparing compounds of the formula (I) comprises reacting a compound of the formula:

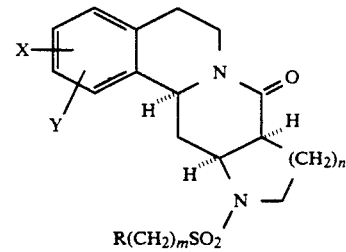

where n, m, R, X and Y are as defined above, with a suitable reducing agent, preferably sodium borohydride in the presence of boron trifluoride etherate.

3. Alternatively, a process for preparing compounds of the formula (I) comprises reacting a compound of the formula:

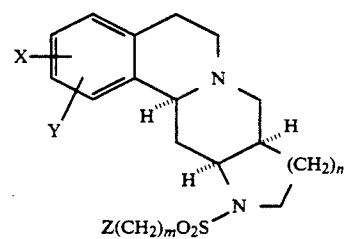

(XII)

where n, m, X, Y and Z are as defined above, with a compound of the formula RM, where R is as defined above and M is an alkali metal.

4. Alternatively, a process for preparing compounds of the formula (I), where R is optionally substituted 4-phenylpiperazin-1-yl, comprises reacting a compound of the formula:

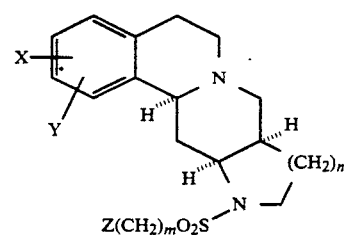

(XII)

where n, m, X, Y and Z are as defined above, with an optionally substituted 4-phenylpiperazine in the presence of a base.

UTILITY AND ADMINISTRATION

General Utility

The compounds of formula (I) and the pharmaceutically acceptable acid addition salts thereof have been found to possess valuable pharmacological properties in the central nervous system and, in particular, have been shown to both selectively block $\alpha_2$-adrenoceptors and partially stimulate 5-$HT_{1A}$ receptors in standard laboratory tests. Accordingly these compounds and pharmaceutically acceptable compositions containing them are useful in the regulation of physiological phenomena related to $\alpha_2$-adrenoceptors and 5-$HT_{1A}$ receptors, including, for example, lowering of blood pressure in normotensive and hypertensive mammals, treatment of disorders of peripheral blood flow, wound healing, inhibition of platelet aggregation, alleviation of male impotence, lowering of intraocular pressure, and palliation of diabetes and its sequelae such as diabetic retinopathy, nephropathy, neuropathy and associated circulatory disturbances. The compounds of formula (I) are particularly useful for the treatment of sexual dysfunction, depression and anxiety.

Testing

Potential for $\alpha_2$-adrenoceptor antagonism is determined in vitro by the method of Brown et al., *Br. J. Pharmacol.*, Vol. 99, pp 803–809 (1990), described in Example 13. Alternatively, such activity may be established by the procedure according to Caroon, J. M. et al., *J. Med. Chem.*, 1982, Vol. 25, 666.

Potential for partial stimulation of 5-$HT_{1A}$ receptors is determined in vitro by the method of Small et al., *Br. J. Pharmacol.*, Vol. 98, pp 756 (1989).

Platelet aggregation inhibition is determined in vitro by the turbidimetric method of Born, *J. Physiol.*, 162, p67 (1962).

Lowering of intraocular pressure is shown in vivo by the method of Moses, R. A., *Tr. Am. Acad. Opth. and Otol.*, Jan-Feb 1962: 88–95.

Alleviation of male impotence is shown in vivo as described by P. Sodersten, D. A. Dammassa and E. R. Smith, *Hormones and Behavior*, Vol. 8, pp 320–334 (1977)

Potential for the treatment of hyperglycemia is shown in vivo as described in Example 18.

Blood pressure lowering activity is shown in vivo by the method described in Example 19.

General Administration

In applying the compounds of this invention to treatment of the above conditions, administration of the active compounds and salts described herein can be via any of the accepted modes of administration, including oral, parenteral and otherwise systemic route of administration. Any pharmaceutically acceptable mode of administration can be used, including solid, semi-solid or liquid dosage forms, such as, for example, tablets, suppositories, pills, capsules, powders, liquids, suspensions, or the like, preferably in unit dosage forms suitable for single administration of precise dosages, or in sustained or controlled release dosage forms for the prolonged administration of the compound at a predetermined rate. The compositions will typically include a conventional pharmaceutical carrier or excipient and an active compound of formula (I) or the pharmaceutically acceptable salts thereof and, in addition, may include other medicinal agents, pharmaceutical agents, carriers, adjuvants, etc.

The amount of active compound administered will of course, be dependent on the subject being treated, the severity of the affliction, the manner of administration and the judgment of the prescribing physician. However, an effective dosage is in the range of 0.001–20 mg/kg/day, preferably 0.01–10 mg/kg/day. For an average 70 kg human, this would amount to 0.07–1400 mg per day, or preferably 0.7–700 mg/day.

For solid compositions, conventional non-toxic solid carriers include, for example, pharmaceutical grades of mannitol, lactose, cellulose derivatives, starch, magnesium stearate, sodium saccharin, talcum, cellulose, glucose, sucrose, magnesium carbonate, and the like may be used. The active compound as defined above may be formulated as suppositories using, for example, polyalkylene glycols, acetylated triglycerides and the like, as the carrier. Liquid pharmaceutically administrable compositions can, for example, be prepared by dissolving, dispersing, etc. an active compound as defined above and optional pharmaceutical adjuvants in a carrier, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, Ph buffering agents and the like, for example, sodium acetate, sorbitan monolaurate, triethanolamine sodium acetate, sorbitan monolaurate, triethanolamine oleate, etc. Actual methods of preparing such dosage forms are known, or will be apparent, to those skilled in this art; for example, see *Remington's Pharmaceutical Sciences*, Mack Publishing Company, Easton, Pa., 15th Edition, 1975. The composition or formulation to be administered will, in any event, contain a quantity of the active compound(s) in an amount effective to alleviate the symptoms of the subject being treated.

Dosage forms or compositions containing active ingredient (compounds of formula (I) or its salts) in the range of 0.25 to 95% with the balance made up from non-toxic carrier may be prepared.

For oral administration, a pharmaceutically acceptable non-toxic composition is formed by the incorporation of any of the normally employed excipients, such as, for example pharmaceutical grades of mannitol, lactose, cellulose derivatives, starch, magnesium stearate, sodium saccharin, talcum, cellulose, glucose, sucrose, magnesium, carbonate, and the like. Such compositions take the form of solutions, suspensions, tablets, pills, capsules, powders, sustained release formulations and the like. Such compositions may contain 1%–95% active ingredient, preferably 5–50%.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolamine oleate, etc.

A more recently devised approach for parenteral administration employs the implantation of a slow-release or sustained-release system, such that a constant level of dosage is maintained. See, e.g., U.S. Pat. No. 3,710,795.

The percentage of active compound contained in such parental compositions is highly dependent on the specific nature thereof, as well as the activity of the compound and the needs of the subject However, percentages of active ingredient of 0.1% to 10% in solution are employable, and will be higher if the composition is a solid which will be subsequently diluted to the above percentages. Preferably the composition will comprise 0.2–2% of the active agent in solution.

For systemic administration via suppository, traditional binders and carriers include, e.g. polyalkalene glycols or triglycerides. Such suppositories may be formed from mixtures containing active ingredient in the range of 0.5%-10%; preferably 1-2%.

In applying the compounds of the invention to treatment of diseases or disorders of the eye which are associated with an abnormally high intraocular pressure, administration may be achieved by any pharmaceutically acceptable mode of administration which provides adequate local concentrations to provide the desired response. These include direct administration to the eye via drops and controlled release inserts or implants, as well as systemic administration as previously described.

Drops and solutions applied directly to the eye are typically sterilized aqueous solutions containing 0.001% to 10%, most preferably 0.005% to 1% of the active ingredient, along with suitable buffer, stabilizer, and preservative. The total concentration of solutes should be such that, if possible, the resulting solution is isotonic with the lacrimal fluid (though this is not absolutely necessary) and has an equivalent pH in the range of pH 6-8. Typical sterilants are phenyl mercuric acetate, thimerosal, chlorobutanol, and benzalkonium chloride. Typical buffer systems and salts are based on, for example, citrate, borate or phosphate; suitable stabilizers include glycerin and polysorbate 80. The aqueous solutions are formulated simply by dissolving the solutes in a suitable quantity of water, adjusting the pH to about 6.8-8.0, making a final volume adjustment with additional water, and sterilizing the preparation using methods known to those in the art.

The dosage level of the resulting composition will, of course, depend on the concentration of the drops, the condition of the subject and the individual magnitude of responses to treatment However, a typical ocular composition could be administered at the rate of about 2-10 drops per day per eye of a 0.1% solution of active ingredient.

The compositions of the present invention may also be formulated for administration in any convenient way by analogy with other topical compositions adapted for use in mammals These compositions may be presented for use in any conventional manner with the aid of any of a wide variety of pharmaceutical carriers or vehicles For such topical administration, a pharmaceutically acceptable non-toxic formulation can take the form of semisolid, liquid, or solid, such as, for example, gels, creams, lotions, solutions, suspensions, ointments, powders, or the like. As an example, the active components may be formulated into a gel using ethanol, propylene glycol, propylene carbonate, polyethylene glycols, diisopropyl adipate, glycerol, water, etc., with appropriate gelling agents, such as Carbomers, Klucels, etc. If desired, the formulation may also contain minor amounts of non-toxic auxiliary substances such as preservatives, antioxidants, pH buffering agents, surface active agents, and the like. Actual methods of preparing such dosage forms are known, or will be apparent, to those skilled in the art; for example, see *Remington's Pharmaceutical Sciences*, Mack Publishing Company, Easton, Pa., 16th Edition, 1980.

The following preparation and examples illustrate the invention but are not intended to limit its scope.

PREPARATION 1

Preparation of Compounds of Formula (IV)

A. Preparation of Formula (IV) where X and Y are hydrogen

Diisopropylamine (28 ml) and 150 ml of tetrahydrofuran were cooled to −65° C. and 125 mL of 1.6M n-butyllithium was added. To the resulting solution was added a solution of 16.2 g of 3,4-dihydroisoquinoline and 38.4 g of 2-methylnicotinic acid diethylamide in tetrahydrofuran. The mixture was allowed to warm to −20° C. and 600 ml of 3N hydrochloric acid was then added followed by 200 ml of water. The mixture was basified with NH$_4$OH and extracted twice with ether. The ether extracts were combined, dried over anhydrous magnesium sulfate and evaporated to a residue, which was dissolved in methanol and acidified with anhydrous HCl in ether. Acetone (50 ml) was added and the mixture was allowed to stand overnight. The crystalline product was collected by filtration, yielding 34 g of (±)-5,6,13,13a-tetrahydroisoquino[2,1-g][1,6]-naphthyridine-8-one hydrochloride, m.p. 220°-222° C.

An additional 7.5 g of the title compound as the free base was obtained by evaporation of the mother liquor followed by partitioning between ether and aqueous NH$_4$OH and silica gel chromatography of the residue obtained from evaporation of the ether, eluting with ethyl acetate, giving the free base, m.p. 72°-73° C.

B. Preparation of Formula (IV) varying X and Y

Similarly, replacing 3,4-dihydroisoquinoline with the following compounds of formula (III):

6-methoxy-3,4-dihydroisoquinoline;
6,7-dimethoxy-3,4-dihydroisoquinoline;
5,8-dimethoxy-3,4-dihydroisoquinoline;
6,7-methylenedioxy-3,4-dihydroisoquinoline; and
6,7-(ethylene-1,2-dioxy)-3,4-dihydroisoquinoline; and
following the procedure of Preparation 1A above, the following compounds of formula (IV) were prepared;

(±)-3-methoxy-5,6,13,13a-tetrahydroisoquino[2,1-g][1,6]naphthyridine-8-one hydrochloride, m.p. 244°-246° C.;

(±)-3-methoxy-5,6,13,13a-tetrahydroisoquino[2,1-g][1,6]naphthyridine-8-one, m.p. 115°-116° C.;

(±)-2,3-dimethoxy-5,6,13,13a-tetrahydroisoquino[2,1-g][1,6]naphthyridine-8-one hydrochloride, m.p. 238°-240° C.;

(±)-1,4-dimethoxy-5,6,13,13a-tetrahydroisoquino[2,1-g][1,6]naphthyridine-8-one hydrochloride;

(±)-2,3-methylenedioxy-5,6,13,13a-tetrahydroisoquino[2,1-g][1,6]naphthyridine-8-one, m.p. 177°-179° C.; and (±)-2,3-(ethylene-1,2-dioxy)-5,6,13,13a-tetrahydroisoquino[2,1-g][1,6]naphthyridine-8-one.

C. Preparation of Formula (IV) varying X and Y

Similarly, replacing 3,4-dihydroisoquinoline with the following compounds of formula (III):

8-methyl-3,4-dihydroisoquinoline;
7-methyl-3,4-dihydroisoquinoline;
6-methyl-3,4-dihydroisoquinoline;
6,7-dimethyl-3,4-dihydroisoquinoline;
6-ethyl-3,4-dihydroisoquinoline;
6-isobutyl-3,4-dihydroisoquinoline;
6-n-hexyl-3,4-dihydroisoquinoline;
8-methoxy-3,4-dihydroisoquinoline;
7-methoxy-3,4-dihydroisoquinoline;
5-methoxy-3,4-dihydroisoquinoline;
6-ethoxy-3,4-dihydroisoquinoline;
6-isobutoxy-3,4-dihydroisoquinoline;
6-n-hexyloxy-3,4-dihydroisoquinoline;
6-hydroxy-3,4-dihydroisoquinoline;
6,7-dihydroxy-3,4-dihydroisoquinoline;

7,8-dimethoxy-3,4-dihydroisoquinoline;
5,8-dimethoxy-3,4-dihydroisoquinoline;
5,6-dimethoxy-3,4-dihydroisoquinoline;
6,7-diethoxy-3,4-dihydroisoquinoline;
6,7-di-n-butoxy-3,4-dihydroisoquinoline;
7,8-methylenedioxy-3,4-dihydroisoquinoline;
5,6-methylenedioxy-3,4-dihydroisoquinoline;
8-chloro-3,4-dihydroisoquinoline;
7-chloro-3,4-dihydroisoquinoline;
6-chloro-3,4-dihydroisoquinoline;
5-chloro-3,4-dihydroisoquinoline;
6-bromo-3,4-dihydroisoquinoline;
6-fluoro-3,4-dihydroisoquinoline;
7-fluoro-3,4-dihydroisoquinoline;
and following the procedure of Preparation 1A above, the following exemplary compounds of formula (IV) are prepared:

(±)-1-methyl-5,6,13,13a-tetrahydroisoquino[2,1-g][1,6]naphthyridine-8-one hydrochloride;
(±)-2-methyl-5,6,13,13a-tetrahydroisoquino[2,1-g][1,6]naphthyridine-8-one hydrochloride;
(±)-3-methyl-5,6,13,13a-tetrahydroisoquino[2,1-g][1,6]naphthyridine-8-one hydrochloride;
(±)-2,3-dimethyl-5,6,13,13a-tetrahydroisoquino[2,1-g][1,6]naphthyridine-8-one hydrochloride;
(±)-3-ethyl-5,6,13,13a-tetrahydroisoquino[2,1-g][1,6]naphthyridine-8-one hydrochloride;
(±)-3-isobutyl-5,6,13,13a-tetrahydroisoquino[2,1-g][1,6]naphthyridine-8-one hydrochloride;
(±)-3-n-hexyl-5,6,13,13a-tetrahydroisoquino[2,1-g][1,6]naphthyridine-8-one hydrochloride;
(±)-1-methoxy-5,6,13,13a-tetrahydroisoquino[2,1-g][1,6]naphthyridine-8-one hydrochloride;
(±)-2-methoxy-5,6,13,13a-tetrahydroisoquino[2,1-g][1,6]naphthyridine-8-one hydrochloride;
(±)-4-methoxy-5,6,13,13a-tetrahydroisoquino[2,1-g][1,6]naphthyridine-8-one hydrochloride;
(±)-3-ethoxy-5,6,13,13a-tetrahydroisoquino[2,1-g][1,6]naphthyridine-8-one hydrochloride;
(±)-3-isobutoxy-5,6,13,13a-tetrahydroisoquino[2,1-g][1,6]naphthyridine-8-one hydrochloride;
(±)-3-n-hexyloxy-5,6,13,13a-tetrahydroisoquino[2,1-g][1,6]naphthyridine-8-one hydrochloride;
(±)-3-hydroxy-5,6,13,13a-tetrahydroisoquino[2,1-g][1,6]naphthyridine-8-one hydrochloride;
(±)-2,3-dihydroxy-5,6,13,13a-tetrahydroisoquino[2,1-g][1,6]naphthyridine-8-one hydrochloride;
(±)-1,2-dimethoxy-5,6,13,13a-tetrahydroisoquino[2,1-g][1,6]naphthyridine-8-one hydrochloride;
(±)-1,4-dimethoxy-5,6,13,13a-tetrahydroisoquino[2,1-g][1,6]naphthyridine-8-one hydrochloride;
(±)-3,4-dimethoxy-5,6,13,13a-tetrahydroisoquino[2,1-g][1,6]naphthyridine-8-one hydrochloride;
(±)-2,3-diethoxy-5,6,13,13a-tetrahydroisoquino[2,1-g][1,6]naphthyridine-8-one hydrochloride;
(±)-2,3-di-n-butoxy-5,6,13,13a-tetrahydroisoquino[2,1-g][1,6]naphthyridine-8-one hydrochloride;
(±)-1,2-methylenedioxy-5,6,13,13a-tetrahydroisoquino[2,1-g][1,6]naphthyridine-8-one hydrochloride;
(±)-3,4-methylenedioxy-5,6,13,13a-tetrahydroisoquino[2,1-g][1,6]naphthyridine-8-one hydrochloride;
(±)-1-chloro-5,6,13,13a-tetrahydroisoquino[2,1-g][1,6]naphthyridine-8-one hydrochloride;
(±)-2-chloro-5,6,13,13a-tetrahydroisoquino[2,1-g][1,6]naphthyridine-8-one hydrochloride;
(±)-3-chloro-5,6,13,13a-tetrahydroisoquino[2,1-g][1,6]naphthyridine-8-one hydrochloride;
(±)-4-chloro-5,6,13,13a-tetrahydroisoquino[2,1-g][1,6]naphthyridine-8-one hydrochloride;
(±)-3-bromo-5,6,13,13a-tetrahydroisoquino[2,1-g][1,6]naphthyridine-8-one hydrochloride;
(±)-2-fluoro-5,6,13,13a-tetrahydroisoquino[2,1-g][1,6]naphthyridine-8-one hydrochloride; and
(±)-3-fluoro-5,6,13,13a-tetrahydroisoquino[2,1-g][1,6]naphthyridine-8-one hydrochloride.

PREPARATION 2

Preparation of Compounds of Formulae (V) and (VI)

A. Preparation of Formulae (V) and (VI) where X and Y are hydrogen

A mixture of 30 g of (±)-5,6,13,13a-tetrahydroisoquino[2,1-g][1,6]naphthyridine-8-one hydrochloride, prepared as shown in Preparation 1 above, and 7.5 g of 5% Rh-Al$_2$O$_3$ in 300 ml of acetic acid was hydrogenated at 50 psi for 42 hours. The catalyst was removed by filtration and the filtrate was concentrated under reduced pressure. The residue was partitioned between methylene chloride and aqueous NH$_4$OH and the methylene chloride layer was separated and the solvent removed under reduced pressure. The residue was purified by silica gel chromatography, eluting with from 5-20% methanol in methylene chloride. The first component eluted was (±)-5,6,8aβ,9,10,11,12,12aβ,13,13aα-decahydroisoquino[2,1-g][1,6]naphthyridin-8-one (9.7 g), (VI), m.p. 105°-106° C.. The second component eluted was (±)-5,6,8aα,9,10,11,12,12aα,13,13aα-decahydroisoquino[2,1-g][1,6]naphthyridin-8-one (11.0 g), (V), m.p. 91°-92° C.

B. Preparation of Formulae (V) and (VI) where X and Y are chosen from hydrogen, methoxy, methylenedioxy and ethylenedioxy Similarly, replacing (±)-5,6,13,13a-tetrahydroisoquino[2,1-g][1,6]naphthyridine-8-one hydrochloride with other compounds of formula (IV), obtained, for example, as described in Preparation 1B, and following the procedure of Preparation 2A above, the following corresponding compounds of formulae (V) and (VI) were prepared:

(±)-3-methoxy-5,6,8aβ,9,10,11,12,12aβ,13,13aα-decahydroisoquino[2,1-g][1,6]naphthyridin-8-one; and
(±)-3-methoxy-5,6,8aα,9,10,11,12,12aα,13,13aα-decahydroisoquino[2,1-g][1,6]naphthyridin-8-one, m.p. 118°-119° C.;
(±)-2,3-dimethoxy-5,6,8aβ,9,10,11,12,12aβ,13,13aα-decahydroisoquino[2,1-g][1,6]naphthyridin-8-one; and
(±)-2,3-dimethoxy-5,6,8aα,9,10,11,12,12aα,13,13aα-decahydroisoquino[2,1-g][1,6]naphthyridin-8-one;
(±)-1,4-dimethoxy-5,6,8aα,9,10,11,12,12aα,13,13aα-decahydroisoquino[2,1-g][1,6]naphthyridin-8-one; and
(±)-1,4-dimethoxy-5,6,8aβ,9,10,11,12,12aβ,13,13aα-decahydroisoquino[2,1-g][1,6]naphthyridin-8-one;
(±)-2,3-methylenedioxy-5,6,8aβ,9,10,11,12,12aβ,13,13aα-decahydroisoquino[2,1-g][1,6]naphthyridin-8-one; and
(±)-2,3-methylenedioxy-5,6,8aα,9,10,11,12,12aα,13,13aα-decahydroisoquino[2,1-g][1,6]naphthyridin-8-one;

(±)-2,3-(ethylene-1,2-dioxy)-5,6,8aβ,9,10,11,12,-12aβ,13,13aα-decahydroisoquino[2,1-g][1,6]naphthyridin-8-one; and (±)-2,3-(ethylene-1,2-dioxy)-5,6,8aα,9,10,11,12,-12aα,13,13aα-decahydroisoquino[2,1-g][1,6]naphthyridin-8-one.

C. Preparation of Formulae (V) and (VI), varying X and Y

Similarly, replacing (±)-5,6,13,13a-tetrahydroisoquino[2,1-g][1,6]naphthyridine-8-one hydrochloride with other compounds of formula (IV), obtained, for example, as described in Preparation 1C, and following the procedure of Preparation 2A above, the following exemplary compounds of formulae (V) and (VI) are prepared:

(±)-1-methyl-5,6,8aβ,9,10,11,12,12aβ,13,13aα-decahydroisoquino[2,1-g][1,6]naphthyridin-8-one; and (±)-1-methyl-5,6,8aα,9,10,11,12,12aα,13,13aα-decahydroisoquino[2,1-g][1,6]naphthyridin-8-one;

(±)-2-methyl-5,6,8aβ,9,10,11,12,12aβ,13,13aα-decahydroisoquino[2,1-g][1,6]naphthyridin-8-one; and (±)-2-methyl-5,6,8aα,9,10,11,12,12aα,13,13aα-decahydroisoquino[2,1-g][1,6]naphthyridin-8-one;

(±)-3-methyl-5,6,8aβ,9,10,11,12,12aβ,13,13aα-decahydroisoquino[2,1-g][1,6]naphthyridin-8-one; and (±)-3-methyl-5,6,8aα,9,10,11,12,12aα,13,13aα-decahydroisoquino[2,1-g][1,6]naphthyridin-8-one;

(±)-2,3-dimethyl-5,6,8aβ,9,10,11,12,12aβ,13,13aα-decahydroisoquino[2,1-g][1,6]naphthyridin-8-one; and (±)-2,3-dimethyl-5,6,8aα,9,10,11,12,12aα,13,13aα-decahydroisoquino[2,1-g][1,6]naphthyridin-8-one;

(±)-3-ethyl-5,6,8aβ,9,10,11,12,12aβ,13,13aα-decahydroisoquino[2,1-g][1,6]naphthyridin-8-one; and (±)-3-ethyl-5,6,8aα,9,10,11,12,12aα,13,13aα-decahydroisoquino[2,1-g][1,6]naphthyridin-8-one;

(±)-3-isobutyl-5,6,8aβ,9,10,11,12,12aβ,13,13aα-decahydroisoquino[2,1-g][1,6]naphthyridin-8-one; and (±)-3-isobutyl-5,6,8aα,9,10,11,12,12aα,13,13aα-decahydroisoquino[2,1-g][1,6]naphthyridin-8-one;

(±)-3-n-hexyl-5,6,8aβ,9,10,11,12,12aβ,13,13aα-decahydroisoquino[2,1-g][1,6]naphthyridin-8-one; and (±)-3-n-hexyl-5,6,8aα,9,10,11,12,12aα,13,13aα-decahydroisoquino[2,1-g][1,6]naphthyridin-8-one;

(±)-1-methoxy-5,6,8aβ,9,10,11,12,12aβ,13,13aα-decahydroisoquino[2,1-g][1,6]naphthyridin-8-one; and (±)-1-methoxy-5,6,8aα,9,10,11,12,12aα,13,13aα-decahydroisoquino[2,1-g][1,6]naphthyridin-8-one;

(±)-2-methoxy-5,6,8aβ,9,10,11,12,12aβ,13,13aα-decahydroisoquino[2,1-g][1,6]naphthyridin-8-one; and (±)-2-methoxy-5,6,8aα,9,10,11,12,12aα,13,13aα-decahydroisoquino[2,1-g][1,6]naphthyridin-8-one;

(±)-4-methoxy-5,6,8aβ,9,10,11,12,12aβ,13,13aα-decahydroisoquino[2,1-g][1,6]naphthyridin-8-one; and (±)-4-methoxy-5,6,8aα,9,10,11,12,12aα,13,13aα-decahydroisoquino[2,1-g][1,6]naphthyridin-8-one;

(±)-3-ethoxy-5,6,8aβ,9,10,11,12,12aβ,13,13aα-decahydroisoquino[2,1-g][1,6]naphthyridin-8-one; and (±)-3-ethoxy-5,6,8aα,9,10,11,12,12aα,13,13aα-decahydroisoquino[2,1-g][1,6]naphthyridin-8-one;

(±)-3-isobutoxy-5,6,8aβ,9,10,11,12,12aβ,13,13aα-decahydroisoquino[2,1-g][1,6]naphthyridin-8-one; and (±)-3-isobutoxy-5,6,8aα,9,10,11,12,12aα,13,13aα-decahydroisoquino[2,1-g][1,6]naphthyridin-8-one;

(±)-3-n-hexyloxy-5,6,8aβ,9,10,11,12,12aβ,13,13aα-decahydroisoquino[2,1-g][1,6]naphthyridin-8-one; and (±)-3-n-hexyloxy-5,6,8aα,9,10,11,12,12aα,13,13-aα-decahydroisoquino[2,1-g][1,6]naphthyridin-8-one;

(±)-3-hydroxy-5,6,8aβ,9,10,11,12,12aβ,13,13aα-decahydroisoquino[2,1-g][1,6]naphthyridin-8-one; and (±)-3-hydroxy-5,6,8aα,9,10,11,12,12aα,13,13aα-decahydroisoquino[2,1-g][1,6]naphthyridin-8-one;

(±)-2,3-dihydroxy-5,6,8aβ,9,10,11,12,12aβ,13,13aα-decahydroisoquino[2,1-g][1,6]naphthyridin-8-one; and (±)-2,3-dihydroxy-5,6,8aα,9,10,11,12,12aα,13,13aα-decahydroisoquino[2,1-g][1,6]naphthyridin-8-one;

(±)-1,2-dimethoxy-5,6,8aβ,9,10,11,12,12aβ,13,13aα-decahydroisoquino[2,1-g][1,6]naphthyridin-8-one; and (±)-1,2-dimethoxy-5,6,8aα,9,10,11,12,12aα,13,13aα-decahydroisoquino[2,1-g][1,6]naphthyridin-8-one;

(±)-1,4-dimethoxy-5,6,8aβ,9,10,11,12,12aβ,13,13aα-decahydroisoquino[2,1-g][1,6]naphthyridin-8-one; and (±)-1,4-dimethoxy-5,6,8aα,9,10,11,12,12aα,13,13aα-decahydroisoquino[2,1-g][1,6]naphthyridin-8-one;

(±)-3,4-dimethoxy-5,6,8aβ,9,10,11,12,12aβ,13,13aα-decahydroisoquino[2,1-g][1,6]naphthyridin-8-one; and (±)-3,4-dimethoxy-5,6,8aα,9,10,11,12,12aα,13,13aα-decahydroisoquino[2,1-q][1,6]naphthyridin-8-one;

(±)-2,3-diethoxy-5,6,8aβ,9,10,11,12,12aβ,13,13aα-decahydroisoquino[2,1-g][1,6]naphthyridin-8-one; and (±)-2,3-diethoxy-5,6,8aα,9,10,11,12,12aα,13,13aα-decahydroisoquino[2,1-g][1,6]naphthyridin-8-one;

(±)-2,3-di-n-butoxy-5,6,8aβ,9,10,11,12,12aβ,13,13aα-decahydroisoquino[2,1-g][1,6]naphthyridin-8-one; and (±)-1,2-methylenedioxy-5,6,8aβ,9,10,11,12,12aβ,13,-13aα-decahydroisoquino[2,1-g][1,6]naphthyridin-8-one; and (±)-1,2-methylenedioxy-5,6,8aα,9,10,11,12,-12aα,13,13aα-decahydroisoquino[2,1-g][1,6]naphthyridin-8-one;

(±)-2-chloro-5,6,8aβ,9,10,11,12,12aβ,13,13aα-decahydroisoquino[2,1-g][1,6]naphthyridin-8-one; and (±)-2-chloro-5,6,8aα,9,10,11,12,12aα,13,13aα-decahydroisoquino[2,1-g][1,6]naphthyridin-8-one;

(±)-3-chloro-5,6,8aβ,9,10,11,12,12aβ,13,13aα-decahydroisoquino[2,1-g][1,6]naphthyridin-8-one; and (±)-3-chloro-5,6,8aα,9,10,11,12,12aα,13,13aα-decahydroisoquino[2,1-g][1,6]naphthyridin-8-one;

(±)-4-chloro-5,6,8aβ,9,10,11,12,12aβ,13,13aα-decahydroisoquino[2,1-g][1,6]naphthyridin-8-one; and (±)-4-chloro-5,6,8aα,9,10,11,12,12aα,13,13aα-decahydroisoquino[2,1-g][1,6]naphthyridin-8-one;

(±)-3-bromo-5,6,8aβ,9,10,11,12,12aβ,13,13aα-decahydroisoquino[2,1-g][1,6]naphthyridin-8-one; and (±)-3-bromo-5,6,8aα,9,10,11,12,12aα,13,13aα-decahydroisoquino[2,1-g][1,6]naphthyridin-8-one;

(±)-2-fluoro-5,6,8aβ,9,10,11,12,12aβ,13,13aα-decahydroisoquino[2,1-g][1,6]naphthyridin-8-one; and (±)-2-fluoro-5,6,8aα,9,10,11,12,12aα,13,13aα-decahydroisoquino[2,1-g][1,6]naphthyridin-8-one;

(±)-3-fluoro-5,6,8aβ,9,10,11,12,12aβ,13,13aα-decahydroisoquino[2,1-g][1,6]naphthyridin-8-one; and (±)-3-fluoro-5,6,8aα,9,10,11,12,12aα,13,13aα-decahydroisoquino[2,1-g][1,6]naphthyridin-8-one.

PREPARATION 3

Preparation of Compounds of Formula (VII)

A. Preparation of Formula (VII) where X and Y are hydrogen

A solution of 9.6 g of (±)-5,6,8aα,9,10,11,12,-12aα,13,13aα-decahydroisoquino[2,1-g][1,6]naphthyridin-8-one (V), prepared as shown in Preparation 2, in 50 ml of tetrahydrofuran was added slowly to a solution of 2.5 g of lithium aluminum hydride in 75 ml of tetrahydrofuran. The resulting mixture was stirred at reflux for 3 hours, cooled, and treated sequentially with 2.5 ml of water, 2.5 ml of 15% sodium hydroxide, and 7.5 ml of water. The mixture was filtered and the filtrate was evaporated to afford 8.8 g of (±)-5,6,8aα,9,10,11,12,-12aα,13,13aα-decahydro-8H-isoquino[2,1-g][1,6]naphthyridine (VII) as a thick oil. The oil was dissolved in ethanol and acidified with anhydrous HCl in ether, from which a dihydrochloride salt was crystallized, m.p. 290°–295° C.

B. Preparation of Formula (VII) where X and Y are chosen from hydrogen, methoxy, methylenedioxy and ethylenedioxy Similarly, replacing (±)-5,6,8aα,9,10,11,12,12aα,13,-13aα-decahydroisoquino[2,1-g][1,6]naphthyridin-8-one with compounds of formula (V), obtained, for example, as described in Preparation 2B, and following the procedure of Preparation 3A above, the following corresponding compounds of formula (VII) were prepared:

(±)-3-methoxy-5,6,8aα,9,10,11,12,12aα,13,13aα-decahydro-8H-isoquino[2,1-g][1,6]naphthyridine;

(±)-2,3-dimethoxy-5,6,8aα,9,10,11,12,12aα,13,13aα-decahydro-8H-isoquino[2,1-g][1,6]naphthyridine;

(±)-1,4-dimethoxy-5,6,8aα,9,10,11,12,12aα,13,13aα-decahydro-8H-isoquino[2,1-g][1,6]naphthyridine;

(±)-2,3-methylenedioxy-5,6,8aα,9,10,11,12,12aα,13,-13aα-decahydro-8H-isoquino[2,1-g][1,6]naphthyridine; and (±)-2,3-(ethylene-1,2-dioxy)-5,6,8aα,9,10,11,1-2,aα,13,13aα-decahydro-8H-isoquino[2,1-g][1,6]naphthyridine;

C. Preparation of Formula (VII), varying X and Y

Similarly, replacing (±)-5,6,8aα,9,10,11,12,12aα,13,-13aα-decahydroisoquino[2,1-g][1,6]naphthyridin-8-one with other compounds of formula (V), obtained, for example, as described in Preparation 2C, and following the procedure of Preparation 3A above, the following exemplary compounds of formula (VII) are prepared:

(±)-1-methyl-5,6,8aα,9,10,11,12,12aα,13,13aα-decahydro-8H-isoquino[2,1-g][1,6]naphthyridine;

(±)-2-methyl-5,6,8aα,9,10,11,12,12aα,13,13aα-decahydro-8H-isoquino[2,1-g][1,6]naphthyridine;

(±)-3-methyl-5,6,8aα,9,10,11,12,12aα,13,13aα-decahydro-8H-isoquino[2,1-g][1,6]naphthyridine;

(±)-2,3-dimethyl-5,6,8aα,9,10,11,12,12aα,13,13aα-decahydro-8H-isoquino[2,1-g][1,6]naphthyridine;

(±)-3-ethyl-5,6,8aα,9,10,11,12,12aα,13,13aα-decahydro-8H-isoquino[2,1-g][1,6]naphthyridine;

(±)-3-isobutyl-5,6,8aα,9,10,11,12,12aα,13,13aα-decahydro-8H-isoquino[2,1-g][1,6]naphthyridine;

(±)-3-n-hexyl-5,6,8aα,9,10,11,12,12aα,13,13aα-decahydro-8H-isoquino[2,1-g][1,6]naphthyridine;

(±)-1-methoxy-5,6,8aα,9,10,11,12,12aα,13,13aα-decahydro-8H-isoquino[2,1-g][1,6]naphthyridine;

(±)-2-methoxy-5,6,8aα,9,10,11,12,12aα,13,13aα-decahydro-8H-isoquino[2,1-g][1,6]naphthyridine;

(±)-4-methoxy-5,6,8aα,9,10,11,12,12aα,13,13aα-decahydro-8H-isoquino[2,1-g][1,6]naphthyridine;

(±)-3-ethoxy-5,6,8aα,9,10,11,12,12aα,13,13aα-decahydro-8H-isoquino[2,1-g][1,6]naphthyridine;

(±)-3-isobutoxy-5,6,8aα,9,10,11,12,12aα,13,13aα-decahydro-8H-isoquino[2,1-g][1,6]naphthyridine;

(±)-3-n-hexyloxy-5,6,8aα,9,10,11,12,12aα,13,13aα-decahydro-8H-isoquino[2,1-g][1,6]naphthyridine;

(±)-3-hydroxy-5,6,8aα,9,10,11,12,12aα,13,13aα-decahydro-8H-isoquino[2,1-g][1,6]naphthyridine;

(±)-2,3-dihydroxy-5,6,8aα,9,10,11,12,12aα,13,13aα-decahydro-8H-isoquino[2,1-g][1,6]naphthyridine;

(±)-1,2-dimethoxy-5,6,8aα,9,10,11,12,12aα,13,13aα-decahydro-8H-isoquino[2,1-g][1,6]naphthyridine;

(±)-1,4-dimethoxy-5,6,8aα,9,10,11,12,12aα,13,13aα-decahydro-8H-isoquino[2,1-g][1,6]naphthyridine;

(±)-3,4-dimethoxy-5,6,8aα,9,10,11,12,12aα,13,13aα-decahydro-8H-isoquino[2,1-g][1,6]naphthyridine;

(±)-2,3-diethoxy-5,6,8aα,9,10,11,12,12aα,13,13aα-decahydro-8H-isoquino[2,1-g][1,6]naphthyridine;

(±)-2,3-di-n-butoxy-5,6,8aα,9,10,11,12,12aα,13,13aα-decahydro-8H-isoquino[2,1-g][1,6]naphthyridine;

(±)-1,2-methylenedioxy-5,6,8aα,9,10,11,12,12aα,13,-13aα-decahydro-8H-isoquino[2,1-g][1,6]naphthyridine;

(±)-2-chloro-5,6,8aα,9,10,11,12,12aα, 13,13aα-decahydro-8H-isoquino[2,1-g][1,6]naphthyridine;

(±)-3-chloro-5,6,8aα,9,10,11,12,12aα,13,13aα-decahydro-8H-isoquino[2,1-g][1,6]naphthyridine;

(±)-4-chloro-5,6,8aα,9,10,11,12,12aα,13,13aα-decahydro-8H-isoquino[2,1-g][1,6]naphthyridine;

(±)-3-bromo-5,6,8aα,9,10,11,12,12aα,13,13aα-decahydro-8H-isoquino[2,1-g][1,6]naphthyridine;

(±)-2-fluoro-5,6,8aα,9,10,11,12,12aα,13,13aα-decahydro-8H-isoquino[2,1-g][1,6]naphthyridine; and (±)-3-fluoro-5,6,8aα,9,10,11,12,12aα,13,13aα-decahydro-8H-isoquino[2,1-g][1,6]naphthyridine.

PREPARATION 4

Preparation of Compounds of Formulae (VIIA) and (VIIB)

Preparation of Formulae (VIIA) and (VIIB) where X is 3-methoxy and Y is hydrogen A. A solution of 1.95 g of (±)-3-methoxy-5,6,8aα,9,10,11,12,12aα,13,13aα-decahydroisoquino[2,1-g][1,6]-naphthyridin-8-one, a compound of formula (V), and 1.0 g of (R)-(+)-α-methylbenzyl isocyanate in 50 ml of methylene chloride was stirred at room temperature for 30 minutes. Solvent was then removed under reduced pressure, and the residue chromatographed on silica gel, using multiple medium pressure chromatography and eluting with 5% methanol in ethyl acetate. The first compound eluted was (8aS,12aS,13aS)-3-methoxy-12-(1-R-phenethylaminocarbonyl)-5,6,8a,9,10,11,12,12a,13,13a-decahydroisoquino[2,1-g][1,6]naphthyridin-8-one, mp 198°–199° C., $[\alpha]_D^{25} = +36.5$ (CHCl$_3$) followed by (8aR,12aR,13aR)-3-methoxy-12-(1-R-phenethylaminocarbonyl)-5,6,8a,9,10,11,12,12a,13,13a-decahydroisoquino[2,1-g][1,6]naphthyridin-8-one, mp 220°–221° C., $[\alpha]_D^{25} = -11.4$ (CHCl$_3$)

B. A solution of 11.5 g of (8aS,12aS,13aS)-3-methoxy-12-(1-R-phenethylaminocarbonyl)-5,6,8a,9,10,11,12,-12a,13,13a-decahydroisoquino[2,1-g][1,6]naphthyridin-8-one, in 50 ml of tetrahydrofuran was added slowly to a solution of 2.0 g of lithium aluminum hydride in 75 ml of tetrahydrofuran. The resulting mixture was stirred at reflux for 2 hours, cooled, and treated sequentially with 2.5 ml of water, 2.5 ml of 15% sodium hydroxide, and 7.5 ml of water. The mixture was filtered and the filtrate was evaporated to afford 8.8 g of (8aR,12aS,13aS)-3-methoxy-12-(1-R-phenethylaminocarbonyl)-5,6,8a,9,10,11,12,12a,13,13a-decahydro-8H-isoquino[2,1-g][1,6]naphthyridine, as a foam. The foam was used as such in the next reaction with no further purification.

C. A solution of 10.5 g of (8aR,12aS,13aS)-3-methoxy-12-(1-R-phenethylaminocarbonyl)-5,6,8a,9,10,11,12,12a,13,13a-decahydro-8H-isoquino[2,1-g][1,6]naphthyridine in 125 ml of 2N sodium n-butoxide in n-butanol was refluxed for 4 hours. After cooling, water was added and the solution acidified with 2N hydrochloric acid. The solution was then washed with ethyl acetate, the aqueous portion basified with aqueous ammonium hydroxide and extracted further with methylene chloride. Solvent was then removed from the extract under reduced pressure and the residue chromatographed on silica gel, eluting with 10-20% methanol in methylene chloride, to give (8aR,12aS,13aS)-3-methoxy-5,6,8a,9,10,11,12,12a,13,13a-decahydro-8H-isoquino[2,1-g][1,6]naphthyridine, a compound of formula (VIIA), mp 125°-127° C., $[\alpha]_D^{25} = -150.7$ (CHCl$_3$)

D. Preparation of Formulae (VIIA) and (VIIB) where X and Y are chosen from hydrogen, methoxy and methylenedioxy Similarly, replacing (±)-3-methoxy-5,6,8a$\alpha$,9,10,11,12,12a$\alpha$,13,13a$\alpha$-decahydroisoquino[2,1-g][1,6]-naphthyridin-8-one with compounds of formula (V), prepared, for example, as shown in Preparation 2B, and following the procedures of Preparation 4A, 4B and 4C above, the following compounds of formula (VIIA) and (VIIB) were prepared:

(8aS,12aR,13aR)-3-methoxy-5,6,8a,9,10,11,12,-12a,13,13a-decahydro-8H-isoquino-[2,1-g][1,6]naphthyridine, mp 125°-127° C., $[\alpha]_D^{25} = +154.5$ (CHCl$_3$).

(8aR,12aS,13aS)-5,6,8a,9,10,11,12,12a,13,13a-decahydro-8H-isoquino[2,1-g][1,6]naphthyridine;

(8aS,12aR,13aR)-5,6,8a,9,10,11,12,12a,13,13a-decahydro-8H-isoquino[2,1-g][1,6]naphthyridine;

(8aR,12aS,13aS)-2,3-methylenedioxy-5,6,8a,9,10,11,12,12a,13,13a-decahydro-8H-isoquino[2,1-g][1,6]naphthyridine; and (8aS,12aR,13aR)-2,3-methylenedioxy-5,6,8a,9,10,11,12,12a,13,13a-decahydro-8H-isoquino[2,1-g][1,6]naphthyridine.

E. Preparation of Formulae (VIIA) and (VIIB), varying X and Y

Similarly, replacing (±)-3-methoxy-5,6,8a$\alpha$,9,10,11,12,12a$\alpha$,13,13a$\alpha$-decahydroisoquino[2,1-g][1,6]-naphthyridin-8-one with other compounds of formula (V), prepared, for example, as shown in Preparation 2B, and following the procedures of Preparation 4A, 4B and 4C above, the following exemplary compounds of formulae (VIIA) and (VIIB) are prepared:

(8aR,12aS,13aS)-2,3-dimethoxy-5,6,8a,9,10,11,12,-12a,13,13a-decahydro-8H-isoquino[2,1-g][1,6]naphthyridine;

(8aS,12aR,13aR)-2,3-dimethoxy-5,6,8a,9,10,11,12,-12a,13,13a-decahydro-8H-isoquino[2,1-g][1,6]naphthyridine;

(8aR,12aS,13aS)-1,4-dimethoxy-5,6,8a,9,10,11,12,-12a,13,13a-decahydro-8H-isoquino[2,1-g][1,6]naphthyridine;

(8aS,12aR,13aR)-1,4-dimethoxy-5,6,8a,9,10,11,12,-12a13,13a-decahydro-8H-isoquino[2,1-g][1,6]naphthyridine;

(8aR,12aS,13aS)-2,3-(ethylene-1,2-dioxy)-5,6,8a,9,10,11,12, 12a,13,13a-decahydro-8H-isoquino[2,1-g][1,6]-naphthyridine;

(8aS,12aR,13aR)-2,3-(ethylene-1,2-dioxy)-5,6,8a,9,10,11,12,12a,13,13a-decahydro-8H-isoquino[2,1-g][1,6]-naphthyridine;

(8aR,12aS,13aS)-1-methyl-5,6,8a,9,10,11,12,12a,13,-13a-decahydro-8H-isoquino[2,1-g][1,6]-naphthyridine;

(8aS,12aR,13aR)-1-methyl-5,6,8a,9,10,11,12,12a,13,13a-decahydro-8H-isoquino[2,1-g][1,6]naphthyridine;

(8aR,12aS,13aS)-2-methyl-5,6,8a,9,10,11,12,12a,13,-13a-decahydro-8H-isoquino[2,1-g][1,6]naphthyridine;

(8aS,12aR,13aR)-2-methyl-5,6,8a,9,10,11,12,12a,13,-13a-decahydro-8H-isoquino[2,1-g][1,6]naphthyridine;

(8aR,12aS,13aS)-3-methyl-5,6,8a,9,10,11,12,12a,13,13a-decahydro-8H-isoquino[2,1-g][1,6]naphthyridine;

(8aS,12aR,13aR)-3-methyl-5,6,8a,9,10,11,12,12a,13,-13a-decahydro-8H-isoquino[2,1-g][1,6]naphthyridine;

(8aR,12aS,13aS)-2,3-dimethyl-5,6,8a,9,10,11,12,-12a,13,13a-decahydro-8H-isoquino[2,1-g][1,6]naphthyridine;

(8aS,12aR,13aR)-2,3-dimethyl-5,6,8a,9,10,11,12,-12a,13,13a-decahydro-8H-isoquino[2,1-g][1,6]naphthyridine; .(8aR,12aS,13aS)-3-ethyl-5,6,8a,9,10,11,12,-12a,13,13a-decahydro-8H-isoquino[2,1-g][1,6]naphthyridine;

(8aS,12aR,13aR)-3-ethyl-5,6,8a,9,10,11,12,12a,13,13a-decahydro-8H-isoquino[2,1-g][1,6]naphthyridine;

(8aR,12aS,13aS)-3-isobutyl-5,6,8a,9,10,11,12,12a,13,-13a-decahydro-8H-isoquino[2,1-g][1,6]naphthyridine;

(8aS,12aR,13aR)-3-isobutyl-5,6,8a,9,10,11,12,12a,13,-13a-decahydro-8H-isoquino[2,1-g][1,6]naphthyridine;

(8aR,12aS,13aS)-3-n-hexyl-5,6,8a,9,10,11,12,12a,13,-13a-decahydro-8H-isoquino[2,1-g][1,6]naphthyridine;

(8aS,12aR,13aR)-3-n-hexyl-5,6,8a,9,10,11,12,12a,13,-13a-decahydro-8H-isoquino[2,1-g][1,6]naphthyridine;

(8aR,12aS,13aS)-1-methoxy-5,6,8a,9,10,11,12,12a,13,-13a-decahydro-8H-isoquino[2,1-g][1,6]naphthyridine;

(8aS,12aR,13aR)-1-methoxy-5,6,8a,9,10,11,12,-12a,13,13a-decahydro-8H-isoquino[2,1-g][1,6]naphthyridine;

(8aR,12aS,13aS)-2-methoxy-5,6,8a,9,10,11,12,12a,13,-13a-decahydro-8H-isoquino[2,1-g][1,6]naphthyridine;

(8aS,12aR,13aR)-2-methoxy-5,6,8a,9,10,11,12,-12a,13,13a-decahydro-8H-isoquino[2,1-g][1,6]naphthyridine;

(8aR,12aS,13aS)-4-methoxy-5,6,8a,9,10,11,12,12a,13,-13a-decahydro-8H-isoquino[2,1-g][1,6]naphthyridine;

(8aS,12aR,13aR)-4-methoxy-5,6,8a,9,10,11,12,-12a,13,13a-decahydro-8H-isoquino[2,1-g][1,6]naphthyridine;

(8aR,12aS,13aS)-3-methoxy-2-methyl-5,6,8a,9,10,11,12,12a,13,13a-decahydro-8H-isoquino[2,1-g][1,6]-naphthyridine;

(8aS,12aR,13aR)-3-methoxy-2-methyl-5,6,8a,9,10,11,12,12a,13,13a-decahydro-8H-isoquino[2,1-g][1,6]-naphthyridine;

(8aR,12aS,13aS)-3-ethoxy-5,6,8a,9,10,11,12,12a,13,-13a-decahydro-8H-isoquino[2,1-g][1,6]naphthyridine;

(8aS,12aR,13aR)-3-ethoxy-5,6,8a,9,10,11,12,12a,13,-13a-decahydro-8H-isoquino[2,1-g][1,6]naphthyridine;

(8aR,12aS,13aS)-3-isopropoxy-5,6,8a,9,10,11,12,-12a,13,13a-decahydro-8H-isoquino[2,1-g][1,6]naphthyridine;

(8aS,12aR,13aR)-3-isopropoxy-5,6,8a,9,10,11,12,-12a,13,13a-decahydro-8H-isoquino[2,1-g][1,6]naphthyridine;

(8aR,12aS,13aS)-3-isobutoxy-5,6,8a,9,10,11,12,-12a,13,13a-decahydro-8H-isoquino[2,1-g][1,6]naphthyridine;

(8aS,12aR,13aR)-3-isobutoxy-5,6,8a,9,10,11,12,-12a,13,13a-decahydro-8H-isoquino[2,1-g][1,6]naphthyridine;

(8aR,12aS,13aS)-3-n-hexyloxy-5,6,8a,9,10,11,12,-12a,13,13a-decahydro-8H-isoquino[2,1-g][1,6]naphthyridine;

(8aS,12aR,13aR)-3-n-hexyloxy-5,6,8a,9,10,11,12,-12a,13,13a-decahydro-8H-isoquino[2,1-g][1,6]naphthyridine;

(8aR,12aS,13aS)-3-hydroxy-5,6,8a,9,10,11,12,12a,13,-13a-decahydro-8H-isoquino[2,1-g][1,6]naphthyridine;

(8aS,12aR,13aR)-3-hydroxy-5,6,8a,9,10,11,12,12a,13,-13a-decahydro-8H-isoquino[2,1-g][1,6]naphthyridine;

(8aR,12aS,13aS)-2,3-dihydroxy-5,6,8a,9,10,11,12,-12a,13,13a-decahydro-8H-isoquino[2,1-g][1,6]naphthyridine;

(8aS,12aR,13aR)-2,3-dihydroxy-5,6,8a,9,10,11,12,-12a,13,13a-decahydro-8H-isoquino[2,1-g][1,6]naphthyridine;

(8aR,12aS,13aS)-1,2-dimethoxy-5,6,8a,9,10,11,12,-12a,13,13a-decahydro-8H-isoquino[2,1-g][1,6]naphthyridine;

(8aS,12aR,13aR)-1,2-dimethoxy-5,6,8a,9,10,11,12,-12a,13,13a-decahydro-8H-isoquino[2,1-g][1,6]naphthyridine;

(8aR,12aS,13aS)-1,4-dimethoxy-5,6,8a,9,10,11,12,-12a,13,13a-decahydro-8H-isoquino[2,1-g][1,6]naphthyridine;

(8aS,12aR,13aR)-1,4-dimethoxy-5,6,8a,9,10,11,12,-12a,13,13a-decahydro-8H-isoquino[2,1-g][1,6]naphthyridine;

(8aR,12aS,13aS)-3,4-dimethoxy-5,6,8a,9,10,11,12,-12a,13,13a-decahydro-8H-isoquino[2,1-g][1,6]naphthyridine;

(8aS,12aR,13aR)-3,4-dimethoxy-5,6,8a,9,10,11,12,-12a,13,13a-decahydro-8H-isoquino[2,1-g][1,6]naphthyridine;

(8aR,12aS,13aS)-2,3-diethoxy-5,6,8a,9,10,11,12,-12a,13,13a-decahydro-8H-isoquino[2,1-g][1,6]naphthyridine;

(8aS,12aR,13aR)-2,3-diethoxy-5,6,8a,9,10,11,12,-12a,13,13a-decahydro-8H-isoquino[2,1g][1,6]naphthyridine;

(8aR,12aS,13aS)-2,3-di-n-butoxy-5,6,8a,9,10,11,12,-12a,13,13a-decahydro-8H-isoquino[2,1-g][1,6]naphthyridine;

(8aS,12aR,13aR)-2,3-di-n-butoxy-5,6,8a,9,10,11,12,-12a, 13,13a-decahydro-8H-isoquino[2,1-g][1,6]naphthyridine;

(8aR,12aS,13aS)-1,2-methylenedioxy-5,6,8a,9,10,11,12,12a,13,13a-decahydro-8H-isoquino[2,1-g][1,6]naphthyridine;

(8aS,12aR,13aR)-1,2-methylenedioxy-5,6,8a,9,10,11,12,12a,13,13a-decahydro-8H-isoquino[2,1-g][1,6]naphthyridine;

(8aR,12aS,13aS)-2-chloro-5,6,8a,9,10,11,12,12a,13,a-decahydro-8H-isoquino[2,1-g][1,6]naphthyridine;

(8aS,12aR,13aR)-2-chloro-5,6,8a,9,10,11,12,12a,13,-13a-decahydro-8H-isoquino[2,1-g][1,6]naphthyridine;

(8aR,12aS,13aS)-3-chloro-5,6,8a,9,10,11,12,12a,13,-13a-decahydro-8H-isoquino[2,1-g][1,6]naphthyridine;

(8aS,12aR,13aR)-3-chloro-5,6,8a,9,10,11,12,12a,13,-13a-decahydro-8H-isoquino[2,1-g][1,6]naphthyridine;

(8aR,12aS,13aS)-4-chloro-5,6,8a,9,10,11,12,12a,13,-13a-decahydro-8H-isoquino[2,1-g][1,6]naphthyridine;

(8aS,12aR,13aR)-4-chloro-5,6,8a,9,10,11,12,12a,13,-13a-decahydro-8H-isoquino[2,1-g][1,6]naphthyridine;

(8aS,12aR,13aR)-3-bromo-5,6,8a,9,10,11,12,12a,13,-13a-decahydro-8H-isoquino[2,1-g][1,6]naphthyridine;

(8aS,12aR,13aR)-3-bromo-5,6,8a,9,10,11,12,12a,13,-13a-decahydro-8H-isoquino[2,1-g][1,6]naphthyridine;

(8aR,12aS,13aS)-2-fluoro-5,6,8a,9,10,11,12,12a,13,-13a-decahydro-8H-isoquino[2,1-g][1,6]naphthyridine;

(8aS,12aR,13aR)-2-fluoro-5,6,8a,9,10,11,12,12a,13,-13a-decahydro-8H-isoquino[2,1-g][1,6]naphthyridine;

(8aR,12aS,13aS)-3-fluoro-5,6,8a,9,10,11,12,12a,13,-13a-decahydro-8H-isoquino[2,1-g][1,6]naphthyridine;

and (8aS,12aR,13aR)-3-fluoro-5,6,8a,9,10,11,12,12a,13,-13a-decahydro-8H-isoquino[2,1-g][1,6]naphthyridine.

PREPARATION 5

Preparation of 2-methylpyrrole-3-carboxylic acid diethylamide

To a solution of 1.6 ml of diethylamine in 30 ml of toluene was added 7.5 ml of 2M trimethylaluminum in hexane, and the mixture stirred for 20 minutes. To this mixture was added 1.53 g of 2-methylpyrrole-3-carboxylic acid ethyl ester, and the reaction mixture refluxed overnight. The mixture was cooled, acidified with aqueous 2N hydrochloric acid and extracted twice with ethyl acetate and three times with methylene chloride. Solvent was removed from the combined extracts under reduced pressure, and the residue was flash chromatographed on silica gel, eluting with 75% ethyl acetate/hexane, giving 1.5 g of 2-methylpyrrole-3-carboxylic acid diethylamide, m.p. 120°–121° C., the compound of formula (b).

PREPARATION 6

Preparation of 1-tert-butoxycarbonyl-2-methylpyrrole-3-carboxylic acid diethylamide, the Compound of Formula (VIII)

To a solution of 3.6 g of 2-methylpyrrole-3-carboxylic acid diethylamide in 25 ml of acetonitrile was added 4.76 g of di-(tert-butyl)dicarbonate and 0.10 g of 4-dimethylaminopyridine. The mixture was stirred for 1 hour, then water added and product extracted with ethyl acetate. The organic layer was washed with water, then solvent removed under reduced pressure. The residue was flash chromatographed on silica gel, eluting with 40% ethyl acetate/hexane, giving 1.5 g of 1-tert-butoxycarbonyl-2-methylpyrrole-3-carboxylic acid diethylamide as an oil, the compound of formula (VIII).

PREPARATION 7

Preparation of Compounds of Formula (IX)

A. Preparation of Formula (IX) where X is 3-methoxy and Y is hydrogen

Diisopropylamine (2.8 ml, 20 mmol) and 75 ml of tetrahydrofuran were cooled to −70° C. and 12.5 ml (20 mmol) of 2.5M n-butyllithium was added. To the resulting solution was added a solution of 4.2 g (15 mmol) of 1-(tert-butoxycarbonyl)-2-methylpyrrole-3-carboxylic acid diethylamide in 10 ml of tetrahydrofuran and the mixture stirred for about 3 minutes. To this mixture was added 2.9 g (18 mmol) of 6-methoxy-3,4-dihydroisoquinoline in 10 ml of tetrahydrofuran. The mixture was stirred for about 30 minutes at −70° C., and then allowed to warm to −30° C. over a period of about 30 minutes. Water (100 ml) was added, and the mixture extracted twice with ethyl acetate. The ethyl acetate extracts were combined, dried over anhydrous magnesium sulfate and evaporated to a residue, which was flash-chromatographed, eluting with 25% ethyl acetate/hexane, to give 3 g of an oil. The oil was crystallized from diethyl ether to give (±)-11-(tert-butoxycarbonyl)-5,6,8,11,12,12a-hexahydro-3-methoxybenzo[a]pyrrole[2,3-e]quinolizin-8-one, m.p. 121°–122° C.

B. Preparation of Formula (IX) where X and Y are 2,3-methylenedioxy

Similarly, replacing 6-methoxy-3,4-dihydro-isoquinoline with 6,7-methylenedioxy-3,4-dihydroisoquinoline, as described in Preparation 1B, and following the procedure of Preparation 7A above, the following compound of formula (IX) was prepared:

(±)-11-(tert-butoxycarbonyl)-5,6,8,11,12,12a-hexahydro-2,3-methylenedioxybenzo[a]pyrrole[2,3-e]-quinolizin-8-one, m.p. 171–172° C.

C. Preparation of Formula (IX), varying X and Y

Similarly, replacing 6-methoxy-3,4-dihydroisoquinoline with other compounds of formula (III) and following the procedure of Preparation 7A above, the following compounds of formula (IX) are prepared:

(±)-11-(tert-butoxycarbonyl)-5,6,8,11,12,12a-hexahydrobenzo[a]pyrrole[2,3-e]quinolizin-8-one;

(±)-11-(tert-butoxycarbonyl)-5,6,8,11,12,12a-hexahydro-1-methoxybenzo[a]pyrrole[2,3-e]quinolizin-8-one;

(±)-11-(tert-butoxycarbonyl)-5,6,8,11,12,12a-hexahydro-2-methoxybenzo[a]pyrrole[2,3-e]quinolizin-8-one;

(±)-11-(tert-butoxycarbonyl)-5,6,8,11,12,12a-hexahydro-4-methoxybenzo[a]pyrrole[2,3-e]quinolizin-8-one;

(±)-11-(tert-butoxycarbonyl)-5,6,8,11,12,12a-hexahydro-3-ethoxybenzo[a]pyrrole[2,3-e]quinolizin-8-one;

(±)-11-(tert-butoxycarbonyl)-5,6,8,11,12,12a-hexahydro-3-isobutoxybenzo[a]pyrrole[2,3-e]quinolizin-8-one;

(±)-11-(tert-butoxycarbonyl)-5,6,8,11,12,12a-hexahydro-3-n-hexyloxybenzo[a]pyrrole[2,3-e]quinolizin-8-one;

(±)-11-(tert-butoxycarbonyl)-5,6,8,11,12,12a-hexahydro-3-hydroxybenzo[a]pyrrole[2,3-e]quinolizin-8-one;

(±)-11-(tert-butoxycarbonyl)-5,6,8,11,12,12a-hexahydro-2,3-dihydroxybenzo[a]pyrrole[2,3-e]quinolizin-8-one;

(±)-11-(tert-butoxycarbonyl)-5,6,8,11,12,12a-hexahydro-2,3-dimethoxybenzo[a]pyrrole[2,3-e]quinolizin-8-one;

(±)-11-(tert-butoxycarbonyl)-5,6,8,11,12,12a-hexahydro-1,4-dimethoxybenzo[a]pyrrole[2,3-e]quinolizin-8-one;

(±)-11-(tert-butoxycarbonyl)-5,6,8,11,12,12a-hexahydro-3,4-dimethoxybenzo[a]pyrrole[2,3-e]quinolizin-8-one;

(±)-11-(tert-butoxycarbonyl)-5,6,8,11,12,12a-hexahydro-2,3-diethoxybenzo[a]pyrrole[2,3-e]quinolizin-8-one;

(±)-11-(tert-butoxycarbonyl)-5,6,8,11,12,12a-hexahydro-2,3-di-n-butoxybenzo[a]pyrrole[2,3-e]-quinolizin-8-one;

(±)-11-(tert-butoxycarbonyl)-5,6,8,11,12,12a-hexahydro-1,2-methylenedioxybenzo[a]pyrrole[2,3-e]-quinolizin-8-one;

(±)-11-(tert-butoxycarbonyl)-5,6,8,11,12,12a-hexahydro-3,4-methylenedioxybenzo[a]pyrrole[2,3-e]-quinolizin-8-one;

(±)-11-(tert-butoxycarbonyl)-5,6,8,11,12,12a-hexahydro-2,3-(ethylene-1,2-dioxy)benzo[a]pyrrole[2,3-e]-quinolizin-8-one;

(±)-11-(tert-butoxycarbonyl)-5,6,8,11,12,12a-hexahydro-1-methylbenzo[a]pyrrole[2,3-e]quinolizin-8-one;

(±)-11-(tert-butoxycarbonyl)-5,6,8,11,12,12a-hexahydro-2-methylbenzo[a]pyrrole[2,3-e]quinolizin-8-one;

(±)-11-(tert-butoxycarbonyl)-5,6,8,11,12,12a-hexahydro-3-methylbenzo[a]pyrrole[2,3-e]quinolizin-8-one;

(±)-11-(tert-butoxycarbonyl)-5,6,8,11,12,12a-hexahydro-2,3-dimethylbenzo[a]pyrrole[2,3-e]quinolizin-8-one;

(±)-11-(tert-butoxycarbonyl)-5,6,8,11,12,12a-hexahydro-3-ethylbenzo[a]pyrrole[2,3-e]quinolizin-8-one;

(±)-11-(tert-butoxycarbonyl)-5,6,8,11,12,12a-hexahydro-3-isobutylbenzo[a]pyrrole[2,3-e]quinolizin-8-one;

(±)-11-(tert-butoxycarbonyl)-5,6,8,11,12,12a-hexahydro-3-n-hexylbenzo[a]pyrrole[2,3-e]quinolizin-8-one;

(±)-11-(tert-butoxycarbonyl)-5,6,8,11,12,12a-hexahydro-1-chlorobenzo[a]pyrrole[2,3-e]quinolizin-8-one;

(±)-11-(tert-butoxycarbonyl)-5,6,8,11,12,12a-hexahydro-2-chlorobenzo[a]pyrrole[2,3-e]quinolizin-8-one;

(±)-11-(tert-butoxycarbonyl)-5,6,8,11,12,12a-hexahydro-3-chlorobenzo[a]pyrrole[2,3-e]quinolizin-8-one;

(±)-11-(tert-butoxycarbonyl)-5,6,8,11,12,12a-hexahydro-3-bromobenzo[a]pyrrole[2,3-e]quinolizin-8-one;

(±)-11-(tert-butoxycarbonyl)-5,6,8,11,12,12a-hexahydro-2-fluorobenzo[a]pyrrole[2,3-e]quinolizin-8-one; and (±)-11-(tert-butoxycarbonyl)-5,6,8,11,12,12a-hexahydro-3-fluorobenzo[a]pyrrole[2,3-e]quinolizin-8-one.

PREPARATION 8

Preparation of Compounds of Formula (X)

A. Preparation of Formula (X) where X is 3-methoxy and Y is hydrogen

A mixture of 15 g of (±)-11-(tert-butoxycarbonyl)-5,6,8,11,12,12a-hexahydro-3-methoxybenzo[a]pyrrolo[2,3-e]quinolizin-8-one, prepared as shown in Preparation 7, and 3.5 g of 5% Rh-Al$_2$O$_3$ in 200 ml of ethanol was hydrogenated at 40 psi for about 4 hours. The catalyst was removed by filtration and the filtrate was concentrated under reduced pressure. The residue was dissolved in 100 ml of methylene chloride and 15 ml of trifluoroacetic acid added. The mixture was stirred for 18 hours at room temperature, and was then partitioned between methylene chloride and aqueous NH$_4$OH, the methylene chloride layer separated and the solvent removed under reduced pressure. The residue was purified by silica gel chromatography, eluting with 1% ammonium hydroxide/10% methanol/methylene chloride to give (±)-(8aα,11aα,12aα)-3-methoxy-5,6,8,8a,9,10,11,11a,12,12a-decahydrobenzo[a]pyrrolo[2,3-e]quinolizin-8-one, (X), m.p. 98°–99° C.

B. Preparation of Formula (X) where X and Y are 2,3-methylenedioxy

Similarly, replacing (±)-11-(tert-butoxycarbonyl)-5,6,8,11,12,12a-hexahydro-3-methoxybenzo[a]pyrrolo[2,3-e]quinolizin-8-one with (±)-11-(tert-butoxycarbonyl)-5,6,8,11,12,12a-hexahydro-2,3-methylenedioxybenzo[a]pyrrole[2,3-e]quinolizin-8-one, prepared, for example, as shown in Preparation 7B, and following the procedure of Preparation 8A above, the following compound of formula (X) was prepared:

(±)-(8aα,11aα,12aα)-2,3-methylenedioxy-5,6,8,8a,9,10,11,11a,12,12a-decahydrobenzo[a]pyrrolo[2,3-e]-quinolizin-8-one, m.p. 175°-176° C.

C. Preparation of Formula (X), varying X and Y

Similarly, replacing (±)-11-(tert-butoxycarbonyl)-5,6,8,11,12,12a-hexahydro-3-methoxybenzo[a]pyrrolo-[2,3-e]quinolizin-8-one with other compounds of formula (IX), prepared, for example, as shown in Preparation 7C, and following the procedure of Preparation 8A above, the following exemplary compounds of formula (X) are prepared:

(±)-(8aα,11aα12aα)-5,6,8,8a,9,10,11,11a,12,12a-decahydrobenzo[a]pyrrolo[2,3-e]quinolizin-8-one;

(±)-(8aα,11aα,12aα)-1-methoxy-5,6,8,8a,9,10,11,-11a,12,12a-decahydrobenzo[a]pyrrolo[2,3-e]quinolizin-8-one;

(±)-(8aα,11aα,12aα)-2-methoxy-5,6,8,8a,9,10,11,-11a,12a-decahydrobenzo[a]pyrrolo[2,3-e]quinolizin-8-one;

(±)-(8aα,11aα,12aα)-4-methoxy-5,6,8,8a,9,10,11,-11a,12, 12a-decahydrobenzo[a]pyrrolo[2,3-e]quinolizin-8-one;

(±)-(8aα,11aα,12aα)-3-ethoxy-5,6,8,8a,9,10,11,-11a,12,12a-decahydrobenzo[a]pyrrolo[2,3-e]quinolizin-8-one;

(±)-(8aα,11aα,12aα)-3-isobutoxy-5,6,8,8a,9,10,11,-11a,12,12a-decahydrobenzo[a]pyrrolo[2,3-e]quinolizin-8-one;

(±)-(8aα, 11aα,12aα)-3-n-hexyloxy-5,6,8,8a,9,10,11,-11a,12,12a-decahydrobenzo[a]pyrrolo[2,3-e]quinolizin-8-one;

(±)-(8aα,11aα,12aα)-3-hydroxy-5,6,8,8a,9,10,11,-11a,12,12a-decahydrobenzo[a]pyrrolo[2,3-e]quinolizin-8-one;

(±)-(8aα,11aα,12aα)-2,3-dihydroxy-5,6,8,8a,9,10,11,-11a,12,12a-decahydrobenzo[a]pyrrolo[2,3-e]quinolizin-8-one;

(±)-(8aα,11aα,12aα)-2,3-dimethoxy-5,6,8,8a,9,10,11,-11a,12,12a-decahydrobenzo[a]pyrrolo[2,3-e]quinolizin-8-one;

(±)-(8aα,11aα,12aα)-1,4-dimethoxy-5,6,8,8a,9,10,11,-11a,12,12a-decahydrobenzo[a]pyrrolo[2,3-e]quinolizin8-one;

(±)-(8aα,11aα,12aα)-3,4-dimethoxy-5,6,8,8a,9,10,11,-11a,12,12a-decahydrobenzo[a]pyrrolo[2,3-e]quinolizin8-one;

(±)-(8aα,11aα,12aα)-2,3-diethoxy-5,6,8,8a,9,10,11,-11a,12,12a-decahydrobenzo[a]pyrrolo[2,3-e]quinolizin8-one;

(±)-(8aα,11aα,12aα)-2,3-di-n-butoxy-5,6,8,8a,9,10,11,12,12a-decahydrobenzo[a]pyrrolo[2,3-e]quinolizin-8-one;

(±)-(8aα,11aα,12aα)-1,2-methylenedioxy-5,6,8,8a,9,10,11,11a,12,12a-decahydrobenzo[a]pyrrolo[2,3-e]-quinolizin- 8-one;

(±)-(8aα,11aα,12aα)-3,4-methylenedioxy-5,6,8,8a,9,10,11,11a,12,12a-decahydrobenzo[a]pyrrolo[2,3-quinolizin-8-one;

(±)-(8aα,11aα,12aα)-2,3-(ethylene-1,2-dioxy)-5,6,8,8a,9,10,11,11a,12,12a-decahydrobenzo[a]pyrrole[2,3-e]quinolizin-8-one;

(±)-(8aα,11aα,12aα)-1-methyl-5,6,8,8a,9,10,11,-11a,12,12a-decahydrobenzo[a]pyrrolo[2,3-e]quinolizin-8-one;

(±)-(8aα,11aα,12aα)-2-methyl-5,6,8,8a,9,10,11,-11a,12,12a-decahydrobenzo[a]pyrrolo[2,3-e]quinolizin-8-one;

(±)-(8aα,11aα,12aα)-3-methyl-5,6,8,8a,9,10,11,-11a,12,12a-decahydrobenzo[a]pyrrolo[2,3-e]quinolizin-8-one;

(±)-(8aα,11aα,12aα)-2,3-dimethyl-5,6,8,8a,9,10,11,-11a,12,12a-decahydrobenzo[a]pyrrolo[2,3-e]quinolizin-8-one;

(±)-(8aα,11aα,12aα)-3-ethyl-5,6,8,8a,9,10,11,11a,12,-12a-decahydrobenzo[a]pyrrolo[2,3-e]quinolizin-8-one;

(±)-(8aα,11aα,12aα)-3-isobutyl-5,6,8,8a,9,10,11,-11a,12,12a-decahydrobenzo[a]pyrrolo[2,3-e]quinolizin8-one;

(±)-(8aα,11aα,12aα)-3-n-hexyl-5,6,8,8a,9,10,11,-11a,12,12a-decahydrobenzo[a]pyrrolo[2,3-e]quinolizin-8-one;

(±)-(8aα,11aα,12aα)-1-chloro-5,6,8,8a,9,10,11,-11a,12,12a-decahydrobenzo[a]pyrrolo[2,3-e]quinolizin-8-one;

(±)-(8aα,11aα,12aα)-2-chloro-5,6,8,8a,9,10,11,-11a,12,12a-decahydrobenzo[a]pyrrolo[2,3-e]quinolizin-8-one;

(±)-(8aα,11aα,12aα)-3-chloro-5,6,8,8a,9,10,11,-11a,12,12a-decahydrobenzo[a]pyrrolo[2,3-e]quinolizin-8-one;

(±)-(8aα,11aα,12aα)-3-bromo-5,6,8,8a,9,10,11,-11a,12,12a-decahydrobenzo[a]pyrrolo[2,3-e]quinolizin-8-one;

(±)-(8aα,11aα, 12aα)-2-fluoro-5,6,8,8a,9,10,11,-11a,12,12a-decahydrobenzo[a]pyrrolo[2,3-e]quinolizin-8-one; and (±)-(8aα,11aα,12aα)-3-fluoro-5,6,8,8a,9,10,11,-11a,12,12a-decahydrobenzo[a]pyrrolo[2,3-e]quinolizin-8-one.

PREPARATION 9

Preparation of Compounds of Formula (XI)

A. Preparation of Formula (XI) where X is 3-methoxy and Y is hydrogen

A solution of 7.6 g of (±)-(8aα,11aα,12aα)-3-methoxy-5,6,8,8a,9,10,11,11a,12,12a-decahydrobenzo[a]-pyrrolo[2,3-e]quinolizin-8-one (X), prepared as shown in Preparation 8, in 125 ml of tetrahydrofuran was added slowly to a solution of 1.0 g of lithium aluminum hydride in 100 ml of tetrahydrofuran. The resulting mixture was stirred at reflux for 3 hours, cooled, and treated sequentially with 2.5 ml of water, 2.5 ml of 15% sodium hydroxide, and 7.5 ml of water. The mixture was filtered and the filtrate was evaporated to afford (±)-(8aα,11aα,12aα)-3-methoxy-5,6,8,8a,9,10,11,-11a,12,12a-decahydrobenzo[a]pyrrolo[2,3-e]quinolizine as an oil. The oil was used in the next reaction with no further purification. B. Preparation of Formula (XI) where X and Y are 2,3-methylenedioxy Similarly, replacing (±)-(8aα,11aα,12aα)-3-methoxy-5,6,8,8a,9,10,11,11a,12,12a-decahydrobenzo[a]pyrrolo[2,3-e]-quinolizin-8-one with (±)-(8aα, 11aα,12aα)-2,3-methylenedioxy-5,6,8,8a,9,10,11,11a,12,12a-decahydrobenzo[a]pyrrolo[2,3-e]quinolizin-8-one, prepared, for example, as shown in Preparation 8B, and following the procedure of Preparation 9A above, the following compound of formula (XI) was prepared:

(±)-(8aα,11aα, 12aα)-2,3-methylenedioxy-5,6,8,8a,9,10,11,11a,12,12a-decahydrobenzo[a]pyrrolo[2,3-e]-quinolizine.

C. Preparation of Formula (XI), varying X and Y

Similarly, replacing (±)-(8aα,11aα,12aα)-3-methoxy-5,6,8,8a,9,10,11,11a,12,12a-decahydrobenzo[a]pyrrolo[2,3-e]-quinolizin-8-one with other compounds of formula (X), prepared, for example, as shown in Preparation 8C, and following the procedure of Preparation 9A above, the following exemplary compounds of formula (XI) are prepared:

(±)-(8aα,11aα,12aα)-5,6,8,8a,9,10,11,11a,12,12a-decahydrobenzo[a]pyrrolo[2,3-e]quinolizine;

(±)-(8aα,11aα,12aα)-1-methoxy-5,6,8,8a,9,10,11,-11a,12,12a-decahydrobenzo[a]pyrrolo[2,3-e]quinolizine;

(±)-(8aα,11aα,12aα)-2-methoxy-5,6,8,8a,9,10,11,-11a,12,12a-decahydrobenzo[a]pyrrolo[2,3-e]quinolizine;

(±)-(8aα,11aα,12aα)-4-methoxy-5,6,8,8a,9,10,11,-11a,12,12a-decahydrobenzo[a]pyrrolo[2,3-e]quinolizine;

(±)-(8aα,11aα,12aα)-3-ethoxy-5,6,8,8a,9,10,11,-11a,12,12a-decahydrobenzo[a]pyrrolo[2,3-e]quinolizine;

(±)-(8aα,11aα, 12aα)-3-isobutoxy-5,6,8,8a,9,10,11,-11a,12,12a-decahydrobenzo a]pyrrolo[2,3-e]quinolizine;

(±)-(8aα,11aα,121α)-3-n-hexyloxy-5,6,8,8a,9,10,11,-11a,12,12a-decahydrobenzo[a]pyrrolo[2,3-e]quinolizine;

(±)-(8aα,11aα,12aα)-3-hydroxy-5,6,8,8a,9,10,11,-11a,12,12a-decahydrobenzo[a]pyrrolo[2,3-e]quinolizine;

(±)-(8aα,11aα,12aα)-2,3=dihydroxy-5,6,8,8a,9,10,11,11a,12,12a-decahydrobenzo[a]pyrrolo[2,3-e]quinolizine;

(±)-(8aα,11aα,12aα)-2,3-dimethoxy-5,6,8,8a,9,10,11,-11a,12,12a-decahydrobenzo[a]pyrrolo[2,3-e]quinolizine;

(±)-(8aα,11aα,12aα)-1,4-dimethoxy-5,6,8,8a,9,10,11,-11a,12,12a-decahydrobenzo[a]pyrrolo[2,3-e]quinolizine;

(±)-(8aα,11aα,12aα)-3,4-dimethoxy-5,6,8,8a,9,10,11,-11a,12,12a-decahydrobenzo[a]pyrrolo[2,3-e]quinolizine;

(±)-(8aα,11aα, 12aα)-2,3-diethoxy-5,6,8,8a,9,10,11,-11a,12,12a-decahydrobenzo[a]pyrrolo[2,3-e]quinolizine;

(±)-(8aα,11aα,12aα)-2,3-di-n-butoxy-5,6,8,8a,9,10,11,11a,12,12a-decahydrobenzo[a]pyrrolo[2,3-e]quinolizine;

(±)-(8aα,11aα,12aα)-1,2-methylenedioxy-5,6,8,8a,9,10,11,11a,12,12a -decahydrobenzo[a]pyrrolo[2,3-e]quinolizine;

(±)-(8aα,11aα,12aα)-3,4-methylenedioxy-5,6,8,8a,9,10,11,11a,12,12a-decahydrobenzo[a]pyrrolo[2,3-e]quinolizine;

(±)-(8aα,11aα,12aα)-2,3-(ethylene-1,2-dioxy)-5,6,8,8a,9,10,11,11a,12,12a-decahydrobenzo[a]pyrrole[2,3-e]quinolizine:

(±)-(8aα,11aα,12aα)-1-methyl-5,6,8,8a,9,10,11,-11a,12,12a-decahydrobenzo[a]pyrrolo[2,3-e]quinolizine;

(±)-(8aα,11aα,12aα)-2-methyl-5,6,8,8a,9,10,11,-11a,12,12a-decahydrobenzo[a]pyrrolo[2,3-e]quinolizine;

(±)-(8aα,11aα,12aα)-3-methyl-5,6,8,8a,9,10,11,-11a,12,12a-decahydrobenzo[a]pyrrolo[2,3-e]quinolizine;

(±)-(8aα,11aα,12aα)-2,3-dimethyl-5,6,8,8a,9,10,11,-11a,12,12a-decahydrobenzo[a]pyrrolo[2,3-e]quinolizine;

(±)-(8aα,11aα,12aα)-3-ethyl-5,6,8,8a,9,10,11,11a,12,-12a-decahydrobenzo[a]pyrrolo[2,3-e]quinolizine;

(±)-(8aα,11aα,12aα)-3-isobutyl-5,6,8,8a,9,10,11,-11a,12,12a-decahydrobenzo[a]pyrrolo[2,3-e]quinolizine;

(±)-(8aα,11aα,12aα)-3-n-hexyl-5,6,8,8a,9,10,11,-11a,12,12a-decahydrobenzo[a]pyrrolo[2,3-e]quinolizine;

(±)-(8aα,11aα,12aα)-1-chloro-5,6,8,8a,9,10,11,-11a,12,12a-decahydrobenzo[a]pyrrolo[2,3-e]quinolizine;

(±)-(8aα,11aα,12aα)-2-chloro-5,6,8,8a,9,10,11,-11a,12,12a-decahydrobenzo[a]pyrrolo[2,3-e]quinolizine;

(±)-(8aα,11aα,12aα)-3-chloro-5,6,8,8a,9,10,11,-11a,12,12a-decahydrobenzo[a]pyrrolo[2,3-e]quinolizine;

(±)-(8aα,11aα,12aα)-3-bromo-5,6,8,8a,9,10,11,-11a,12,12a-decahydrobenzo[a]pyrrolo[2,3-e]quinolizine;

(±)-(8aα,11aα,12aα)-2-fluoro-5,6,8,8a,9,10,11,-11a,12,12a-decahydrobenzo[a]pyrrolo[2,3-e]quinolizine; and (±)-(8aα,11aα,12aα)-3-fluoro-5,6,8,8a,9,10,11,-11a,12,12a-decahydrobenzo[a]pyrrolo[2,3-e]quinolizine.

PREPARATION 10

Preparation of Compounds of Formula (XII)

A. Preparation of Formula (XII) where m is 3, X is 3-methoxy, Y is hydrogen, Z is chloro and n is 1

A solution of 7.2 g of (±)-(8aα,11aα,12aα)-3-methoxy-5,6,8,8a,9,10,11,11a,12,12a-decahydrobenzo[a]pyrrolo[2,3-e]quinolizine (XI), prepared as shown in Preparation 9, and 7 ml of triethylamine in 150 ml of methylene chloride was cooled to 0° C., and 5.5 g of 3-chloropropanesulfonyl chloride in 50 ml of dichloromethane added. An exothermic reaction was observed. The resulting mixture was stirred at O° C. for 30 minutes, then washed with dilute ammonium hydroxide. The methylene chloride layer was separated and the solvent removed under reduced pressure. The residue was purified by silica gel chromatography, eluting with 50% ethyl acetate/hexane, to afford (±)-(8aα,11aα,1-2aα)-3-methoxy-11-(3-chloropropanesulfonyl)-5,6,8,8a,9,10,11,11a,12,12a-decahydrobenzo[a]pyrrolo[2,3-e]quinolizine, a compound of formula (XII) where n is 1, as an oil.

B. Preparation of Formula (XII) where m is 3, X is 3-methoxy, Y is hydrogen, Z is chloro and n is 2

Similarly, replacing (±)-(8aα,11aα,12aα)-3-methoxy-5,6,8,8a,9,10,11,11a,12,12a-decahydrobenzo[a]pyrrolo[2,3e]quinolizine with (8aR,12aS,13aS)-3-methoxy-5,6,8a,9,10,11,12,12a,13,13a-decahydro-8H-isoquino[2,1-g][1,6]naphthyridine, prepared, for example, as shown in Preparation 4, and following the procedure of Preparation 10A above, the following compound of formula (XII) where n is 2 was prepared:

(8aR,12aS,13aS)-3-methoxy-12-(3-chloropropanesulfonyl)-5,6,8a,9,10,11,12,12a,13,13a-decahydro-8H-isoquino[2,1-g][1,6]naphthyridine as an oil, which was converted to the hydrochloride salt in ethanol/ether mixture by treatment with anhydrous hydrochloric acid, to give (8aR,12aS,13aS)-3-methoxy-12-(3-chloropropanesulfonyl)-5,6,8a,9,10,11,12,12a,13,13a-decahydro-8H-isoquino[2,1-g][1,6]naphthyridine hydrochloride, m.p. 203°-205° C., $[\alpha]_D^{25} = +28.7°$ (c=0.55, CH$_3$OH).

C. Preparation of Formula (XII) where n is 1, varying m, X, Y and Z

Similarly, optionally replacing (±)-(8aα,11aα,12aα)-3-methoxy-5,6,8,8a,9,10,11,11a,12,12a-decahydrobenzo[a]pyrrolo[2,3-e]quinolizine with racemic compounds of formula (XI), prepared, for example, as shown in Preparation 9, or single enantiomers of a compound of formula (XI), optionally replacing 3-chloropropanesulfonyl chloride with an appropriate haloalkylsulfonyl halide of formula ZASO$_2$Z, where Z is chloro and A is lower alkylene of 1-6 carbon atoms, and following the procedure of Preparation 10A above, the following compounds of formula (XII) where n is 1 are prepared in racemic or optically active form:

(8aα,11aα,12aα)-3-methoxy-11-(chloromethanesulfonyl)-5,6,8,8a,9,10,11,11a,12,12a-decahydrobenzo[a]pyrrolo[2,3-e]-quinolizine;

(8aα,11aα,12aα)-3-methoxy-11-(2-chloroethanesulfonyl)-5,6,8,8a,9,10,11,11a,12,12a-decahydrobenzo[a]pyrrolo[2,3-e]-quinolizine;

(8aα,11aα,12aα)-3-methoxy-11-(4-chlorobutanesulfonyl)-5,6,8,8a,9,10,11,11a,12,12a-decahydrobenzo[a]pyrrolo[2,3-e]-quinolizine;

(8aα,11aα,12aα)-3-methoxy-11-(3-chloro-2-methylpropanesulfonyl)-5,6,8,8a,9,10,11,11a,12,12a-decahydrobenzo[a]pyrrolo[2,3-e]quinolizine;

(8aα,11aα,12aα)-3-methoxy-11-(3-chloro-1,2-dimethylpropanesulfonyl)-5,6,8,8a,9,10,11,11a,12,12a-decahydrobenzo[a]pyrrolo[2,3-e]quinolizine;

(8aα,11aα,12aα)-3-methoxy-11-(6-chlorohexanesulfonyl)-5,6,8,8a,9,10,11,11a,12,12a-decahydrobenzo[a]pyrrolo[2,3-e]quinolizine;

(8aα,11aα,12aα)-11-(3-chloropropanesulfonyl)-5,6,8,8a,9,10,11,11a,12,12a-decahydrobenzo[a]pyrrolo[2,3-e]quinolizine;

(8aα,11aα,12aα)-1-methoxy-11-(3-chloropropanesulfonyl)-5,6,8,8a,9,10,11,11a,12,12a-decahydrobenzo[a]pyrrolo[2,3-e]quinolizine;

(8aα,11aα,12aα)-2-methoxy-11-(3-chloropropanesulfonyl)-5,6,8,8a,9,10,11,11a,12,12a-decahydrobenzo[a]pyrrolo[2,3-e]quinolizine;

(8aα,11aα,12aα)-4-methoxy-11-(3-chloropropanesulfonyl)-5,6,8,8a,9,10,11,11a,12,12a-decahydrobenzo[a]pyrrolo[2,3-e]quinolizine;

(8aα,11aα,12aα)-3-ethoxy-11-(3-chloropropanesulfonyl)-5,6,8,8a,9,10,11,11a,12,12a-decahydrobenzo[a]pyrrolo[2,3-e]quinolizine;

(8aα,11aα,12aα)-3-isobutoxy-11-(3-chloropropanesulfonyl)-5,6,8,8a,9,10,11,11a,12,12a-decahydrobenzo[a]pyrrolo[2,3-e]quinolizine;

(8aα,11aα,12aα)-3-n-hexyloxy-11-(3-chloropropanesulfonyl)-5,6,8,8a,9,10,11,11a,12,12a-decahydrobenzo[a]pyrrolo[2,3-e]quinolizine;

(8aα,11aα,12aα)-3-hydroxy-11-(3-chloropropanesulfonyl)-5,6,8,8a,9,10,11,11a,12,12a-decahydrobenzo[a]pyrrolo[2,3-e]quinolizine;

(8aα,11aα,12aα)-2,3-dihydroxy-11-(3-chloropropanesulfonyl)-5,6,8,8a,9,10,11,11a,12,12a-decahydrobenzo[a]pyrrolo[2,3-e]quinolizine;

(8aα,11aα,12aα)-2,3-dimethoxy-11-(3-chloropropanesulfonyl)-5,6,8,8a,9,10,11,11a,12,12a-decahydrobenzo[a]pyrrolo[2,3-e]quinolizine;

(8aα,11aα,12aα)-1,4-dimethoxy-11-(3-chloropropanesulfonyl)-5,6,8,8a,9,10,11,11a,12,12a-decahydrobenzo[a]pyrrolo[2,3-e]quinolizine;

(8aα,11aα,12aα)-3,4-dimethoxy-11-(3-chloropropanesulfonyl)-5,6,8,8a,9,10,11,11a,12,12a-decahydrobenzo[a]pyrrolo[2,3-e]quinolizine;

(8aα,11aα,12aα)-2,3-diethoxy-11-(3-chloropropanesulfonyl)-5,6,8,8a,9,10,11,11a,12,12a-decahydrobenzo[a]pyrrolo[2,3-e]quinolizine;

(8aα,11aα,12aα)-2,3-di-n-butoxy-11-(3-chloropropanesulfonyl)-5,6,8,8a,9,10,11,11a,12,12a-decahydrobenzo[a]pyrrolo[2,3-e]quinolizine;

(8aα,11aα,12aα)-2,3-dihexyloxy-11-(3-chloropropanesulfonyl)-5,6,8,8a,9,10,11,11a,12,12a-decahydrobenzo[a]pyrrolo[2,3-e]quinolizine;

(8aα,11aα,12aα)-2,3-methylenedioxy-11-(3-chloropropanesulfonyl)-5,6,8,8a,9,10,11,11a,12,12a-decahydrobenzo[a]pyrrolo[2,3-e]quinolizine;

(8aα,11aα,12aα)-2,3-methylenedioxy-11-(chloromethanesulfonyl)-5,6,8,8a,9,10,11,11a,12,12a-decahydrobenzo[a]pyrrolo[2,3-e]quinolizine;

(8aα,11aα,12aα)-2,3-methylenedioxy-11-(2-chloroethanesulfonyl)-5,6,8,8a,9,10,11,11a,12,12a-decahydrobenzo[a]pyrrolo[2,3-e]quinolizine;

(8aα,11aα,12aα)-2,3-methylenedioxy-11-(4-chlorobutanesulfonyl)-5,6,8,8a,9,10,11,11a,12,12a-decahydrobenzo[a]pyrrolo[2,3-e]quinolizine;

(8aα,11aα,12aα)-2,3-methylenedioxy-11-(3-chloro-2-methylpropanesulfonyl)-5,6,8,8a,9,10,11,11a,12,12a-decahydrobenzo[a]pyrrolo[2,3-e]quinolizine;

(8aα,11aα,12aα)-2,3-methylenedioxy-11-(3-chloro-1,2-dimethylpropanesulfonyl)-5,6,8,8a,9,10,11,11a,12,12a-decahydrobenzo[a]pyrrolo[2,3-e]quinolizine;

(8aα,11aα,12aα)-2,3-methylenedioxy-11-(6-chlorohexanesulfonyl)-5,6,8,8a,9,10,11,11a,12,12a-decahydrobenzo[a]pyrrolo[2,3-e]quinolizine;

(8aα,11aα,12aα)-1,2-methylenedioxy-11-(3-chloropropanesulfonyl)-5,6,8,8a,9,10,11,11a,12,12a-decahydrobenzo[a]pyrrolo[2,3-e]quinolizine;

(8aα,11aα,12aα)-3,4-methylenedioxy-11-(3-chloropropanesulfonyl)-5,6,8,8a,9,10,11,11a,12,12a-decahydrobenzo[a]pyrrolo[2,3-e]quinolizine;

(8aα,11aα,12aα)-2,3-(ethylene-1,2-dioxy)-11-(3-chloropropanesulfonyl)-5,6,8,8a,9,10,11,11a,12,12a-decahydrobenzo[a]pyrrole[2,3-e]quinolizine;

(8aα,11aα,12aα)-1-methyl-11-(3-chloropropanesulfonyl)-5,6,8,8a,9,10,11,11a,12,12a-decahydrobenzo[a]pyrrolo[2,3-e]quinolizine;

(8aα,11aα,12aα)-2-methyl-11-(3-chloropropanesulfonyl)-5,6,8,8a,9,10,11,11a,12,12a-decahydrobenzo[a]pyrrolo[2,3-e]quinolizine;

(8aα,11aα,12aα)-3-methyl-11-(3-chloropropanesulfonyl)-5,6,8,8a,9,10,11,11a,12,12a-decahydrobenzo[a]pyrrolo[2,3-e]quinolizine;

(8aα,11aα,12aα)-2,3-dimethyl-11-(3-chloropropanesulfonyl)-5,6,8,8a,9,10,11,11a,12,12a-decahydrobenzo[a]pyrrolo[2,3-e]quinolizine;

(8aα,11aα,12aα)-3-ethyl-11-(3-chloropropanesulfonyl)-5,6,8,8a,9,10,11,11a,12,12a-decahydrobenzo[a]pyrrolo[2,3-e]quinolizine;

(8aα,11aα,12aα)-3-isobutyl-11-(3-chloropropanesulfonyl)-5,6,8,8a,9,10,11,11a,12,12a-decahydrobenzo[a]pyrrolo[2,3-e]quinolizine;

(8aα,11aα,12aα)-3-n-hexyl-11-(3-chloropropanesulfonyl)-5,6,8,8a,9,10,11,11a,12,12a-decahydrobenzo[a]pyrrolo[2,3-e]quinolizine;

(8aα,11aα,12aα)-1-chloro-11-(3-chloropropanesulfonyl)-5,6,8,8a,9,10,11,11a,12,12a-decahydrobenzo[a]pyrrolo[2,3-e]quinolizine;

(8aα,11aα,12aα)-2-chloro-11-(3-chloropropanesulfonyl)-5,6,8,8a,9,10,11,11a,12,12a-decahydrobenzo[a]pyrrolo[2,3-e]quinolizine;

(8aα,11aα,12aα)-3-chloro-11-(3-chloropropanesulfonyl)-5,6,8,8a,9,10,11,11a,12,12a-decahydrobenzo[a]pyrrolo[2,3-e]quinolizine;

(8aα,11aα,12aα)-3-bromo-11-(3-chloropropanesulfonyl)-5,6,8,8a,9,10,11,11a,12,12a-decahydrobenzo[a]pyrrolo[2,3-e]quinolizine;

(8aα,11aα,12aα)-2-fluoro-11-(3-chloropropanesulfonyl)-5,6,8,8a,9,10,11,11a,12,12a-decahydrobenzo[a]pyrrolo[2,3-e]quinolizine; and (8aα,11aα,12aα)-3-fluoro-11-(3-chloropropanesulfonyl)-5,6,8,8a,9,10,11,11a,12,12a-decahydrobenzo[a]pyrrolo[2,3-e]quinolizine.

D. Preparation of Formula (XII) where n is 2, varying m, X, Y and Z

Similarly, optionally replacing (±)-(8aα,11aα,12aα)-3-methoxy-5,6,8,8a,9,10,11,11a,12,12a-decahydrobenzo[a]pyrrolo[2,3-e]quinolizine with an appropriate racemic compound of formula (VII), prepared, for example, as shown in Preparation 3, or an individual enantiomer of formula (VIIA) or (VIIB), prepared, for example, as shown in Preparation 4, and optionally replacing 3-chloropropanesulfonyl chloride with an appropriate haloalkylsulfonyl halide of formula ZASO$_2$Z, where Z is chloro and A is lower alkylene of 1-6 carbon atoms, and following the procedures of Preparation 10A above, the following compounds of formula (XII) where n is 2 are prepared in racemic or optically active form:

(8aα,12aα,13aα)-3-methoxy-12-(chloromethanesulfonyl)-5,6,8a,9,10,11,12,12a,13,13a-decahydro-8H-isoquino[2,1-g][1,6]naphthyridine;

(8aα,12aα,13aα)-3-methoxy-12-(2-chloroethanesulfonyl)-5,6,8a,9,10,11,12,12a,13,13a-decahydro-8H-isoquino[2,1-g][1,6]naphthyridine;

(8aα,12aα,13aα)-3-methoxy-12-(4-chlorobutanesulfonyl)-5,6,8a,9,10,11,12,12a,13,13a-decahydro-8H-isoquino[2,1-g][1,6]naphthyridine;

- (8aα,12aα,13aα)-3-methoxy-12-(3-chloro-2-methylpropanesulfonyl)-5,6,8a,9,10,11,12,12a,13,13a-decahydro-8H-isoquino[2,1-g][1,6]naphthyridine;

(8aα,12aα,13aα)-3-methoxy-12-(3-chloro-1,2-dimethylpropanesulfonyl)-5,6,8a,9,10,11,12,12a,13,13a-decahydro-8H-isoquino[2,1-g][1,6]naphthyridine;

(8aα,12aα,13aα)-3-methoxy-12-(6-chlorohexanesulfonyl)-5,6,8a,9,10,11,12,12a,13,13a-decahydro-8H-isoquino[2,1-g][1,6]naphthyridine;

(8aα,12aα,13aα)-12-(3-chloropropanesulfonyl)-5,6,8a,9,10,11,12,12a,13,13a-decahydro-8H-isoquino[2,1-g][1,6]naphthyridine;

(8aα,12aα,13aα)-2,3-methylenedioxy-12-(3-chloropropanesulfonyl)-5,6,8a,9,10,11,12,12a,13,13a-decahydro-8H-isoquino[2,1-g][1,6]naphthyridine (8aα,12aα,13aα)-2,3-methylenedioxy-12-(chloromethanesulfonyl)-5,6,8a,9,10,11,12,12a,13,13a-decahydro-8H-isoquino[2,1-g][1,6]naphthyridine;

(8aα,12aα,13aα)-2,3-methylenedioxy-12-(2-chloroethanesulfonyl)-5,6,8a,9,10,11,12,12a,13,13a-decahydro-8H-isoquino[2,1-g][1,6]naphthyridine;

(8aα,12aα,13aα)-2,3-methylenedioxy-12-(4-chlorobutanesulfonyl)-5,6,8a,9,10,11,12,12a,13,13a-decahydro-8H-isoquino[2,1-g][1,6]naphthyridine;

(8aα,12aα,13aα)-2,3-methylenedioxy-12-(3-chloro-2-methylpropanesulfonyl)-5,6,8a,9,10,11,12,12a,13,13a-decahydro-8H-isoquino[2,1-g][1,6]naphthyridine;

(8aα,12aα,13aα)-2,3-methylenedioxy-12-(3-chloro-1,2-dimethylpropanesulfonyl)-5,6,8a,9,10,11,12,12a,13,13a-decahydro-8H-isoquino[2,1-g][1,6]naphthyridine;

(8aα,12aα,13aα)-2,3-methylenedioxy-12-(6-chlorohexanesulfonyl)-5,6,8a,9,10,11,12,12a,13,13a-decahydro-8H-isoquino[2,1-q][1,6]naphthyridine;

(8aα,12aα,13aα)-2,3-dimethoxy-12-(3-chloropropanesulfonyl)-5,6,8a,9,10,11,12,12a,13,13a-decahydro-8H-isoquino[2,1-g][1,6]naphthyridine;

(8aα,12aα,13aα)-1,4-dimethoxy-12-(3-chloropropanesulfonyl)-5,6,8a,9,10,11,12,12a,13,13a-decahydro-8H-isoquino]2,1-g][1,6]naphthyridine;

(8aα,12aα,13aα)-2,3-(ethylene-1,2-dioxy)-12-(3-chloropropanesulfonyl)-5,6,8a,9,10,11,12,12a,13,13a-decahydro-8H-isoquino[2,1-g][1,6]naphthyridine;

(8aα,12aα,13aα)-1-methyl-12-(3-chloropropanesulfonyl)-5,6,8a,9,10,11,12,12a,13,13a-decahydro-8H-isoquino[2,1-g][1,6]naphthyridine;

(8aα,12aα,13aα)-2-methyl-12-(3-chloropropanesulfonyl)-5,6,8a,9,10,11,12,12a,13,13a-decahydro-8H-isoquino[2,1-g][1,6]naphthyridine;

(8aα,12aα,13aα)-3-methyl-12-(3-chloropropanesulfonyl)-5,6,8a,9,10,11,12,12a,13,13a-decahydro-8H-isoquino[2,1-g][1,6]naphthyridine;

(8aα,12aα,13aα)-2,3-dimethyl-12-(3-chloropropanesulfonyl)-5,6,8a,9,10,11,12,12a,13,13a-decahydro-8H-isoquino[2,1-g][1,6]naphthyridine;

(8aα,12aα,13aα)-3-ethyl-12-(3-chloropropanesulfonyl)-5,6,8a,9,10,11,12,12a,13,13a-decahydro-8H-isoquino[2,1-g][1,6]naphthyridine;

(8aα,12aα,13aα)-3-isobutyl-12-(3-chloropropanesulfonyl)-5,6,8a,9,10,11,12,12a,13,13a-decahydro-8H-isoquino[2,1-g][1,6]naphthyridine;

(8aα,12aα,13aα)-3-n-hexyl-12-(3-chloropropanesulfonyl)-5,6,8a,9,10,11,12,12a,13,13a-decahydro-8H-isoquino[2,1-g][1,6]naphthyridine;

(8aα,12aα,13aα)-1-methoxy-12-(3-chloropropanesulfonyl)-5,6,8a,9,10,11,12,12a,13,13a-decahydro-8H-isoquino[2,1-g][1,6]naphthyridine;

(8aα,12aα,13aα)-2-methoxy-12-(3-chloropropanesulfonyl)-5,6,8a,9,10,11,12,12a,13,13a-decahydro-8H-isoquino[2,1-g][1,6]naphthyridine;

(8aα,12aα,13aα)-4-methoxy-12-(3-chloropropanesulfonyl)-5,6,8a,9,10,11,12,12a,13,13a-decahydro-8H-isoquino[2,1-g][1,6]naphthyridine;

(8aα,12aα,13aα)-3-methoxy-12-methyl-12-(3-chloropropanesulfonyl)-5,6,8a,9,10,11,12,12a,13,13a-decahydro-8H-isoquino[2,1-g][1,6]naphthyridine;

(8aα,12aα,13aα)-3-ethoxy-12-(3-chloropropanesulfonyl)-5,6,8a,9,10,11,12,12a,13,13a-decahydro-8H-isoquino[2,1-g][1,6]naphthyridine;

(8aα,12aα,13aα)-3-isopropoxy-12-(3-chloropropanesulfonyl)-5,6,8a,9,10,11,12,12a,13,13a-decahydro-8H-isoquino[2,1-g][1,6]naphthyridine;

(8aα,12aα,13aα)-3-n-hexyloxy-12-(3-chloropropanesulfonyl)-5,6,8a,9,10,11,12,12a,13,13a-decahydro-8H-isoquino[2,1-g][1,6]naphthyridine;

(8aα,12aα,13aα)-3-hydroxy-12-(3-chloropropanesulfonyl)-5,6,8a,9,10,11,12,12a,13,13a-decahydro-8H-isoquino[2,1-g][1,6]naphthyridine;

(8aα,12aα,13aα)-2,3-dihydroxy-12-(3-chloropropanesulfonyl)-5,6,8a,9,10,11,12,12a,13,13a-decahydro-8H-isoquino[2,1-g][1,6]naphthyridine;

(8aα,12aα,13aα)-1,2-dimethoxy-12-(3-chloropropanesulfonyl)-5,6,8a,9,10,11,12,12a,13,13a-decahydro-8H-isoquino[2,1-g][1,6]naphthyridine;

(8aα,12aα,13aα)-1,4-dimethoxy-12-(3-chloropropanesulfonyl)-5,6,8a,9,10,11,12,12a,13,13a-decahydro-8H-isoquino[2,1-g][1,6]naphthyridine;

(8aα,12aα,13aα)-3,4-dimethoxy-12-(3-chloropropanesulfonyl)-5,6,8a,9,10,11,12,12a,13,13a-decahydro-8H-isoquino[2,1-g][1,6]naphthyridine;

(8aα,12aα,13aα)-2,3-diethoxy-12-(3-chloropropanesulfonyl)-5,6,8a,9,10,11,12,12a,13,13a-decahydro-8H-isoquino[2,1-g][1,6]naphthyridine;

(8aα,12aα,13aα)-2,3-di-n-butoxy-12-(3-chloropropanesulfonyl)-5,6,8a,9,10,11,12,12a,13,13a-decahydro-8H-isoquino[2,1-g][1,6]naphthyridine;

(8aα,12aα,13aα)-1,2-methylenedioxy-12-(3-chloropropanesulfonyl)-5,6,8a,9,10,11,12,12a,13,13a-decahydro-8H-isoquino[2,1-g][1,6]naphthyridine;

(8aα,12aα,13aα)-2-chloro-12-(3-chloropropanesulfonyl)-5,6,8a,9,10,11,12,12a,13,13a-decahydro-8H-isoquino[2,1-g][1,6]naphthyridine;

(8aα,12aα,13aα)-3-chloro-12-(3-chloropropanesulfonyl)-5,6,8a,9,10,11,12,12a,13,13a-decahydro-8H-isoquino[2,1-g][1,6]naphthyridine;

(8aα,12aα,13aα)-4-chloro-12-(3-chloropropanesulfonyl)-5,6,8a,9,10,11,12,12a,13,13a-decahydro-8H-isoquino[2,1-g][1,6]naphthyridine;

(8aα,12aα,13aα)-3-bromo-12-(3-chloropropanesulfonyl)-5,6,8a,9,10,11,12,12a,13,13a-decahydro-8H-isoquino[2,1-g][1,6]naphthyridine;

(8aα,12aα,13aα)-3-fluoro-12-(3-chloropropanesulfonyl)-5,6,8a,9,10,11,12,12a,13,13a-decahydro-8H-isoquino[2,1-g][1,6]naphthyridine; and (8aα,12aα,13aα)-2-fluoro-12-(3-chloropropanesulfonyl)-5,6,8a,9,10,11,12,12a,13,13a-decahydro-8H-isoquino[2,1-g][1,6]naphthyridine.

EXAMPLE 1

Preparation of Compounds of Formula (I)

A. Preparation of Formula (I) where m is 3, X is 3-methoxy, Y is hydrogen, R is 8-azaspiro[4.5]decan-7,9-dione and n is 2

To a solution of 0.835 g of 8-azaspiro[4.5]decan-7,9-dione in 10 ml of DMF was added 0.24 g of sodium hydride, and the mixture stirred at 80° C. for 2 hours. Then 1.0 g of (8aR,12aS,13aS)-3-methoxy-12-(3-chloropropanesulfonyl)-5,6,8a,9,10,11,12,12a,13,13a-decahydro-8H-isoquino[2,1-g][1,6]naphthyridine was added, plus a catalytic amount of sodium iodide, and the mixture stirred at 80° C. for 16 hours. After cooling, the solution was acidified with 2N hydrochloric acid and then washed with ethyl acetate, the aqueous portion basified with aqueous ammonium hydroxide and extracted further with diethylether. The solvent was then dried over sodium sulfate and evaporated under reduced pressure. The residue was flash chromatographed on silica gel, eluting with 50% ethyl acetate in hexane, to give (8aR,12aS,13aS)-3-methoxy-12-[8-(3-propyl)-8-azaspiro[4.5]decan-7,9-dione]sulfonyl-5,6,8a,9,10,11,12,12a,13,13a-decahydro-8H-isoquino[2,1-g][1,6]naphthyridine as an oil, a compound of formula (I) where n is 2.

To prepare the hydrochloride salt, the free base was dissolved in 25 ml of acetone and a solution of about 7.5N anhydrous hydrochloric acid in ethanol added until pH 1 was attained (about 1 ml). The solution was seeded with a crystal of the hydrochloride salt, and the mixture cooled to −20° C. overnight. The precipitated crystals were filtered off and dried under vacuum, giving (8aR,12aS,13aS)-3-methoxy-12-[8-(3-propyl)-8-azaspiro[4.5]decan-7,9-dione]sulfonyl-5,6,8a,9,10,11,12,12a,13,13a-decahydro-8H-isoquino[2,1-g][1,6]naphthyridine hydrochloride; m.p. 145°–170° C., $[\alpha]_D^{25} = -18.6°$ (c=0.65, pyridine).

B. Preparation of Formula (I) where m is 3, X is 3-methoxy, Y is hydrogen and n is 2, varying R Similarly, replacing 8-azaspiro[4.5]decan-7,9-dione with a compound of formula RH, where R is as defined above, and following the procedure of Example 1A above, the following compounds of formula (I) where n is 2 were prepared:

(8aR,12aS,13aS)-3-methoxy-12-[3-(3,3-dimethylglutarimid-1-yl)propanesulfonyl]-5,6,8a,9,10,11,12,12a,13,13a-decahydro-8H-isoquino[2,1-g][1,6]naphthyridine hydrochloride, m.p. 150°–152° C., $[\alpha]_D^{25} = +20.7°$ (c=1.275, CH$_3$OH).

(8aR,12aS,13aS)-3-methoxy-12-{3-[2-(benzoisothiazole-3(2H)-one-1,1-dioxide)]propanesulfonyl}-5,6,8a,9,10,11,12,12a,13,13a-decahydro-8H-isoquino[2,1-g][1,6]naphthyridine hydrochloride, m.p. 230°–231° C., $[\alpha]_D^{25} = +11.8°$ (c=0.98, DMSO/H$_2$O 2:1).

C. Preparation of Formula (I) varying m, n, R, X and Y

Similarly, optionally replacing (8aR,12aS,13aS)-3-methoxy-12-(3-chloropropanesulfonyl)-5,6,8a,9,10,11,12,12a,13,13a-decahydro-8H-isoquino-2,1-g][1,6]naphthyridine with the appropriate compound of formula (XII) where n is 1 or 2, as a racemic mixture or a single stereoisomer, prepared for example as shown in Preparation 10C and 10D, and optionally replacing 8-azaspiro[4.5]decan-7,9-dione with the appropriate compound of formula RH, where R is as defined above, and following the procedure in Example 1A above, the following compounds of formula (I) where n is 1 or 2 are prepared in racemic or optically active form:

(8aα,11aα,12aα)-3-methoxy-11-[8-(3-propyl)-8-azaspiro[4.5]decan-7,9-dione]sulfonyl-5,6,8,8a,9,10,11,11a,12,12a-decahydrobenzo[a]pyrrolo[2,3-e]quinolizine;

(8aα,11aα,12aα)-3-methoxy-11-[3-(3,3-dimethylglutarimid-1-yl)propanesulfonyl]-5,6,8,8a,9,10,11,11a,12,12a-decahydrobenzo[a]pyrrolo[2,3-e]quinolizine;

(8aα,11aα,12aα)-3-methoxy-11-{3-[2-(benzoisothiazole-3(2H)-one-11-dioxide)]propanesulfonyl}-5,6,8,8a,9,10,11,11a,12,12a-decahydrobenzo[a]pyrrolo-2,3-e]quinolizine;

(8aα,11aα,12aα)-3-methoxy-11-[3-(4-phenylpiperazinyl)propanesulfonyl]-5,6,8,8a,9,10,11,11a,12,12a-decahydrobenzo[a]pyrrolo[2,3-e]quinolizine;

(8aα,11aα,12aα)-11-[8-(3-propyl)-8-azaspiro-4.5]decan-7,9-dione]sulfonyl-5,6,8,8a,9,10,11,11a,12,12a-decahydrobenzo[a]pyrrolo[2,3-e]quinolizine;

(8aα,11aα,12aα)-11-[3-(3,3-dimethylglutarimidy-1)propanesulfonyl]-5,6,8,8a,9,10,11,11a,12,12a-decahydrobenzo[a]pyrrolo[2,3-e]quinolizine;

(8aα,11aα,12aα)-11-{3-[2-(benzoisothiazole-3(2H)one-1,1-dioxide)]propanesulfonyl}-5,6,8,8a,9,10,11,11a,12,12a-decahydrobenzo[a]pyrrolo-[2,3-e]quinolizine;

(8aα11aα,12aα)-11-[3-(4-phenylpiperazin-1-yl)propanesulfonyl]-5,6,8,8a,9,10,11,11a,12,12a-decahydrobenzo[a]pyrrolo[2,3-e]quinolizine;

(8aα,11aα,12aα)-3-hydroxy-11-[8-(3-propyl)-8azaspiro[4.5]decan-7,9-dione]sulfonyl-5,6,8,8a,9,10,11,-

11a,12,12a-decahydrobenzo[a]pyrrolo[2,3-e]quinolizine;

(8aα,11aα,12aα)-3-hydroxy-11-[3-(3,3-dimethylglutarimid-1-yl)propanesulfonyl]-5,6,8,8a,9,10,11,-11a,12,12a-decahydrobenzo[a]pyrrolo[2,3-e]quinolizine;

(8aα,11aα,12aα)-3-hydroxy-11-{3-[2-(benzoisothiazole-3(2H)-one-1,1-dioxide)]propanesulfonyl}-5,6,8,8a,9,10,11,11a,12,12a-decahydrobenzo[a]pyrrolo[2,3-e]quinolizine;

(8aα,11aα,12aα)-3-hydroxy-11-[3-(4-phenylpiperazin-1-yl)propanesulfonyl]-5,6,8,8a,9,10,11,11a,12,12a-decahydrobenzo[a]pyrrolo[2,3-e]quinolizine;

(8aα,11aα,12aα)-3-methyl-11-[8-(3-propyl)-8-azaspiro[4.5]decan-7,9-dione]sulfonyl-5,6,8,8a,9,10,11,-11a,12,12a-decahydrobenzo[a]pyrrolo[2,3-e]quinolizine;

(8aα,11aα,12aα)-3-methyl-11-[3-(3,3-dimethylglutarimid-1-yl)propanesulfonyl]-5,6,8,8a,9,10,11,-11a,12,12a-decahydrobenzo[a]pyrrolo[2,3-e]quinolizine;

(8aα,11aα,12aα)-{3-methyl-11-(3-[2-(benzoisothiazole-3(2H)-one-1,1-dioxide)]propanesulfonyl}-5,6,8,8a,9,10,11,11a,12,12a-decahydrobenzo[a]pyrrolo[2,3-e]quinolizine;

(8aα,11aα,12aα)-3-methyl-11-[3-(4-phenylpiperazin-1-yl)propanesulfonyl]-5,6,8,8a,9,10,11,11a,12,12a-decahydrobenzo[a]pyrrolo[2,3-e]quinolizine;

(8aα,11aα,12aα)-3-chloro-11-[8-(3-propyl)-8azaspiro[4.5]decan-7,9-dione]sulfonyl-5,6,8,8a,9,10,11,-11a,12,12a-decahydrobenzo[a]pyrrolo[2,3-e]quinolizine;

(8aα,11aα,12aα)-3-chloro-11-[3-(3,3-dimethylglutarimid-1-yl)propanesulfonyl]-5,6,8,8a,9,10,11,-11a,12,12a-decahydrobenzo[a]pyrrolo[2,3-e]quinolizine;

(8aα,11aα,12aα)-{3-chloro-11-(3-[2-(benzoisothiazole-3(2H)-one-1,1-dioxide)]propanesulfonyl)}-5,6,8,8a,9,10,11,11a,12,12a-decahydrobenzo[a]pyrrolo[2,3-e]quinolizine;

(8aα,11aα,12aα)-3-chloro-11-[3-(4-phenylpiperazin-1-yl)propanesulfonyl]-5,6,8,8a,9,10,11,11a,12,12a-decahydrobenzo[a]pyrrolo[2,3-e]quinolizine;

(8aα,11aα,12aα)-2,3-methylenedioxy-11-[8-(3-propyl)-8-azaspiro[4.5]decan-7,9-dione]sulfonyl-5,6,8,8a,9,10,a,12,12a-decahydrobenzo[a]pyrrolo[2,3-e]quinolizine;

(8aα,11aα,12aα)-2,3-methylenedioxy-11-[3-(3,3-dimethylglutarimid-1-yl)propanesulfonyl]-5,6,8,8a,9,10,11,11a,12,12a-decahydrobenzo[a]pyrrolo[2,3-e]quinolizine;

(8aα,11aα,12aα)-2,3-methylenedioxy-11-{3-[2-(benzoisothiazole-3(2H)-one-1,1-dioxide)]propanesulfonyl}-5,6,8,8a,9,10,11,11a,12,12a-decahydrobenzo[a]pyrrolo[2,3-e]quinolizine;

(8aα,11aα,12aα)-2,3-methylenedioxy-11-[3-(4-phenylpiperazin-1-yl)propanesulfonyl]-5,6,8,8a,9,10,11,11a,12,12a-decahydrobenzo[a]pyrrolo[2,3-e]quinolizine;

(8aα,11aα,12aα)-3-methoxy-11-[8-(3-ethyl)-8azaspiro[4.5]decan-7,9-dione]sulfonyl-5,6,8,8a,9,10,11a,12,-12a-decahydrobenzo[a]pyrrolo[2,3-e]quinolizine;

(8aα,11aα,12aα)-3-methoxy-11-[3-(3,3-dimethylglutarimid-1-yl)ethanesulfonyl]-5,6,8,8a,9,10,11,11a,12,-12a-decahydrobenzo[a]pyrrolo[2,3-e]quinolizine;

(8aα,11aα,12aα)-3-methoxy-11-{3-[2-(benzoisothiazole-3(2H)-one-1,1-dioxide)]ethanesulfonyl}-5,6,8,8a,9,10,11,11a,12,12a-decahydrobenzo[a]pyrrolo[2,3-e]quinolizine;

(8aα,11aα,12aα)-3-methoxy-11-[3-(4-phenylpiperazinyl)ethanesulfonyl]-5,6,8,8a,9,10,11,11a,12,12a-decahydrobenzo[a]pyrrolo[2,3-e]quinolizine;

(8aα,11aα,12aα)-3-methoxy-11-[8-(3-butyl)-8azaspiro[4.5]decan-7,9-dione]sulfonyl-5,6,8,8a,9,10,11,-11a,12,12a-decahydrobenzo[a]pyrrolo[2,3-e]quinolizine;

(8aα11aα,12aα)-3-methoxy-11-[3-(3,3-dimethylglutarimid-1-yl)butanesulfonyl]-5,6,8,8a,9,10,11,11a,12,-12a-decahydrobenzo[a]pyrrolo[2,3-e]quinolizine;

(8aα11aα,12aα)-{3-methoxy-11-{3-[2-(benzoisothiazole-3(2H)-one-1,1-dioxide)]butanesulfonyl}-5,6,8,8a,9,10,11,11a,12,12a-decahydrobenzo[a]pyrrolo[2,3-e]quinolizine;

(8aα,11aα,12aα)-3-methoxy-11-[3-(4-phenylpiperazin-1-yl)butanesulfonyl]-5,6,8,8a,9,10,11,11a,12,12a-decahydrobenzo[a]pyrrolo[2,3-e]quinolizine;

(8aα,12aα,13aα)-3-methoxy-12-[3-(4-phenylpiperazin-1-yl)propanesulfonyl]-5,6,8a,9,10,11,12,12a,13,13a-decahydro-8H-isoquino[2,1-g][1,6]naphthyridine;

(8aα,12aα,13aα)-12-[8-(3-butyl)-8-azaspiro[4.5]decan-7,9-dione]sulfonyl-5,6,8a,9,10,11,12,12a-13,13a-decahydro-8H-isoquino[2,1-g][1,6]naphthyridine;

(8aα,12aα,13aα)-12-[3-(3,3-dimethylglutarimid-1yl)-propanesulfonyl]-5,6,8a,9,10,11,12,12a,13,13a-decahydro-8H-isoquino[2,1-g][1,6]naphthyridine;

(8aα,12aα,13aα)-12-{3-[2-(benzoisothiazole-3(2H)-one-1,1-dioxide)]propanesulfonyl]-5,6,8a,9,10,11,12,12a,13,13a-decahydro-8H-isoquino[2,1-g][1,6]naphthyridine;

(8aα,12aα,13aα)-12-[3-(4-phenylpiperazin-1yl)-propanesulfonyl]-5,6,8a,9,10,11,12,12a,13,13a-decahydro-8H-isoquino[2,1-g][1,6]naphthyridine;

(8aα,12aα,13aα)-3-methyl-12-[8-(3-butyl)-8-azaspiro[4.5]decan-7,9-dione]sulfonyl-5,6,8a,9,10,11,12,-12a,13,13a-decahydro-8H-isoquino[2,1-g][1,6]naphthyridine;

(8aα,12aα,13aα)-3-methyl-12-[3-(3,3-dimethylglutarimid-1-yl)propanesulfonyl]-5,6,8a,9,10,11,12,-12a,13,13a-decahydro-8H-isoquino[2,1-g][1,6]naphthyridine;

(8aα,12aα,13aα)-3-methyl-12-{3-[2-(benzoisothiazole-3(2H)-one-1,1-dioxide)]propanesulfonyl]-5,6,8a,9,10,11,12,12a,13,13a-decahydro-8H-isoquino[2,1-q][1,6]naphthyridine;

(8aα,12aα,13aα)-3-methyl-12-[3-(4-phenylpiperazin-1yl)propanesulfonyl]-5,6,8a,9,10,11,12,12a,13,13a-decahydro-8H-isoquino[2,1-g][1,6]naphthyridine;

(8aα,12aα,13aα)-3-hydroxy-12-[8-(3-butyl)-8azaspiro-[4.5]decan-7,9-dione]sulfonyl-5,6,8a,9,10,11,12,-12a,13,13a-decahydro-8H-isoquino[2,1-g][1,6]naphthyridine;

(8aα,12aα,13aα)-3-hydroxy-12-[3-(3,3-dimethylglutarimid-1-yl)propanesulfonyl]-5,6,8a,9,10,11,12,-12a,13,13a-decahydro-8H-isoquino[2,1-q][1,6]naphthyridine;

(8aα,12aα,13aα)-3-hydroxy-12-(3-[2-(benzoisothiazole-3(2H)-one-1,1-dioxide)]propanesulfonyl]5,6-,8a,9,10,11,12,12a,13,13a-decahydro-8H-isoquino[2,1-g][1,6]naphthyridine;

(8aα,12aα,13aα)-3-hydroxy-12-[3-(4-phenylpiperazin-1-yl)propanesulfonyl]-5,6,8a,9,10,11,12,12a,13,13a-decahydro-8H-isoquino[2,1-g][1,6]naphthyridine;

(8aα,12aα,13aα)-3-chloro-12-[8-(3-butyl)-8-azaspiro-[4.5]decan-7,9-dione]sulfonyl-5,6,8a,9,10,11,12,12a13,-13a-decahydro-8H-isoquino[2,1-g][1,6]naphthyridine;

(8aα,12aα,13aα)-3-chloro-12-[3-(3,3-dimethyl-glutarimid-1-yl)propanesulfonyl]-5,6,8a,9,10,11,12,-12a,13,13a=decahydro-8H-isoquino[2,1-g][1,6]-naphthyridine;

(8aα,12aα,13aα)-3-chloro-12-{3-[2-(benzoisothiazole-3(2H)-one-1,1-dioxide)]propanesulfonyl]-5,6,8a,9,10,11,12,12a,13,13a-decahydro-8H-isoquino[2,1-g][1,6]naphthyridine;

(8aα,12aα,13aα)-3-chloro-12-[3-(4-phenylpiperazin-1-yl)propanesulfonyl]-5,6,8a,9,10,11,12,12a,13,13a-decahydro-8H-isoquino[2,1-g][1,6]naphthyridine;

(8aα,12aα,13aα)-2,3-methylenedioxy-12-[8-(3-butyl)-8-azaspiro[4.5]decan-7,9-dione]sulfonyl-5,6,8a,9,10,11,12,12a,13,13a-decahydro-8H-isoquino[2,1-g][1,6]naphthyridine;

(8aα,12aα,13aα)-2,3-methylenedioxy-12-[3-(3,3-dimethylglutarimid-1-yl)propanesulfonyl]-5,6,8a,9,10,11,12,12a,13,13a-decahydro-8H-isoquino[2,1-g][1,6]naphthyridine;

(8aα,12aα,13aα)-2,3-methylenedioxy-12-{3--[2-(benzoisothiazole-3(2H)-one-1,1-dioxide)]-propanesulfonyl]-5,6,8a,9,10,11,12,12a,13,13a-decahydro-8H-isoquino[2,1-g][1,6]naphthyridine;

(8aα,12aα,13aα)-2,3-methylenedioxy-12-[3-(4-phenylpiperazin-1-yl)propanesulfonyl]-5,6,8a,9,10,11,12,12a,13,13a-decahydro-8H-isoquino[2,1-g][1,6]naphthyridine;

(8aα,12aα,13aα)-3-methoxy-12-[8-(3-ethyl)-8-azaspiro[4.5]decan-7,9-dione]sulfonyl-5,6,8a,9,10,11,12,-12a,13,13a-decahydro-8H-isoquino[2,1-g][1,6]naphthyridine;

(8aα,12aα,13aα)-3-methoxy-12-[3-(3,3-dimethyl-glutarimid-1-yl)ethanesulfonyl]-5,6,8a,9,10,11,12,-12a,13,13a-decahydro-8H-isoquino[2,1-g][1,6]naphthyridine;

(8aα,12aα,13aα)-3-methoxy-12-{3-[2-(benzoisothiazole-3(2H)-one-1,1-dioxide)]ethanesulfonyl]5,6-,8a,9,10,11,12,12a,13,13a-decahydro-8H-isoquino[2,1-g][1,6]naphthyridine;

(8aα,12aα,13aα)-3-methoxy-12-[3-(4-phenylpiperazin-1-yl)ethanesulfonyl]-5,6,8a,9,10,11,12,12a,13,13a=-decahydro-8H-isoquino[2,1-g][1,6]naphthyridine;

(8aα,12aα,13aα)-3-methoxy-12-[8-(3-butyl)-8-azaspiro[4.5]decan-7,9-dione]sulfonyl-5,6,8a,9,10,11,12,-12a,13,13a-decahydro-8H-isoquino[2,1-g][1,6]naphthyridine;

(8aα,12aα,13aα)-3-methoxy-12-[3-(3,3-dimethyl-glutarimid-1-yl)butanesulfonyl]-5,6,8a,9,10,11,12,-12a,13,13a-decahydro-8H-isoquino[2,1-g][1,6]naphthyridine;

(8aα,12aα,13aα)-3-methoxy-12-{3-[2-(benzoisothiazole-3(2H)-one-1,1-dioxide)]butanesulfonyl]5,6-,8a,9,10,11,12,12a,13,13a-decahydro-8H-isoquino[2,1-g][1,6]naphthyridine; and (8aα,12aα,13aα)-3-methoxy-12-[3-(4-phenylpiperazin-1-yl)butanesulfonyl]-5,6,8a,9,10,11,12,12a,13,13a-decahydro-8H-isoquino[2,1-g][1,6]naphthyridine.

EXAMPLE 2

Alternative Preparation of Compounds of Formula (I) where R is Optionally Substituted Phenylpiperazin-1-yl A. Preparation of Formula (I) where m is 3, X is 3-methoxy, Y is hydrogen, R is 4-(2-methoxyphenyl)piperazin-1-yl and n is 2

A mixture of 1.8 g of 4-(2-methoxyphenyl)piperazine, 1.8 g of (8aR,12aS,13aS)-3-methoxy-12-(3-chloropropane-sulfonyl)-5,6,8a,9,10,11,12,12a,13,13a-decahydro-8H-isoquino[2,1-g][1,6]naphthyridine and 1 ml of triethylamine in 10 ml of DMF was stirred at 90° C. for 16 hours. The temperature was then raised to 120° C. for 8 hours and stirring continued. After cooling, the solution was acidified with 2N hydrochloric acid and then washed with ethyl acetate, the aqueous portion basified with aqueous ammonium hydroxide and extracted further with diethylether. The solvent was then dried over sodium sulfate and evaporated under reduced pressure. The residue was flash chromatographed on silica gel, eluting with ethyl acetate, to give (8aR,12aS,13aS)-3-methoxy-12-{3-[4-(2-methoxyphenyl)piperazin-1-yl]propanesulfonyl}-5,6,8a,9,10,11,12,12a,13,13a-decahydro-8H-isoquino[2,1-g][1,6]naphthyridine, a compound of formula (I).

The hydrochloride salt was crystallized from ethanol/ether mixture, m.p. 190°-192° C., $[\alpha]_D^{25} = +27.7°$ (c=0.47, CH$_3$OH).

B. Preparation of Formula (I) where R is 4-(2-methoxyphenyl)piperazin-1-yl, varying m, n, X and Y Similarly, optionally replacing (8aR,12aS,13aS)-3-methoxy-12-(3-chloropropanesulfonyl)-5,6,8a,9,10,11,12,12a,13,13a-decahydro-8H-isoquino-2,1-g][1,6]naphthyridine with a compound of formula (XII) where n is 1 or 2, as a racemic mixture or a single stereoisomer, prepared for example as shown in Preparation 10C and 10D, and optionally replacing 4-(2-methoxyphenyl)piperazine with an optionally substituted 4-phenylpiperazine, and following the procedure of Example 2A above, those compounds of formula (I) where n is 1 or 2 and R is an optionally substituted 4-phenylpiperazine are prepared in racemic or optically active form, for example (±)-(8aα,12aα,13aα)-3-methoxy-12-{3-[4-(2-methoxyphenyl)piperazin-1-yl]propanesulfonyl}-5,6,8a,9,10,11,12,12a,13,13a-decahydro-8H-isoquino[2,1-g][1,6]-naphthyridine.

EXAMPLE 3

Preparation of Acid Addition Salts of Compounds of Formula (I)

A. Conversion of (8aR,12aS,13aS)-3-methoxy-12-3-(8-azaspiro-7,9-dione-[4.5]decan-8-yl)propanesulfonyl-5,6,8a,9,10,11,12,-12a,13,13a-decahydro-8H-isoquino[2,1-g][1,6]naphthyridine to its hydrochloride salt To a solution of 80 g of (8aR,12aS,13aS)-3-methoxy-12-[3-(8-azaspiro-7,9-dione[4.5]decan-8yl]propanesulfonyl-5,6,8a,9,10,11,12,12a,13,13a-decahydro-8H-isoquino-[2,1-g][1,6]-naphthyridine in 600 ml of acetone was added about 20 ml of a solution of anhydrous 7.5N hydrochloric acid in ethanol, until the pH was about 1. The solution was seeded with a crystal of the hydrochloride salt, and kept at −20° C. overnight. The white crystals were filtered off under nitrogen, washed with 50 ml of acetone and dried under vacuum, yielding (8aR,12aS,13aS)-3-methoxy-12-[3-(8-azaspiro-7,9dione[4.5]decan-8-yl)propanesulfonyl-5,6,8a,9,10,11,12,a,13,13a-decahydro-8H-isoquino[2,1-g][1,6]naphthyridine hydrochloride.

B. In a similar manner, all compounds of formula (I) in free base form may be converted to the acid addition salts by treatment with the appropriate acid, for example, hydrochloric acid, hydrobromic acid, sulfuric acid, nitric acid, phosphoric acid, acetic acid, propionic acid, glycolic acid, pyruvic acid, oxalic acid, malonic acid, salicylic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid, and the like.

EXAMPLE 4

Conversion of a salt of (8aR,12aS,13aS)-3-methoxy-12-[3-(8-azaspiro-7,9-dione-[4.5]decan-8-yl]propanesulfonyl-5,6,8a,9,10,-11,12,12a,13,13a-decahydro-8H-isoquino[2,1-q][11,6]naphthyridine to the free base (8aR,12aS,13aS)-3-methoxy-12-[3-(8-azaspiro-7,9-dione-[4.5]decan-8-yl]propanesulfonyl-5,6,8a,9,10,11,12,12a,13,13a-decahydro-8H-isoquino[2,1-g][1,6]naphthyridine hydrochloride suspended in 50 ml of ethyl acetate is stirred with excess dilute aqueous potassium carbonate solution until the salt is completely dissolved. The organic layer is then separated, washed twice with water, dried over magnesium sulfate and evaporated to yield (8aR,12aS,13aS)-3-methoxy-12-[3-(8-azaspiro-7,9-dione-[4.5]decan-8-yl]propanesulfonyl-5,6,8a,9,10,11,12,12a,13,13a-decahydro-8H-isoquino[2,1-g][1,6]-naphthyridine.

In a similar manner the acid addition salts of all compounds of formula (I) may be converted to the corresponding compounds in free base form.

EXAMPLE 5

Direct interchange of acid addition salts of (8aR,12aS,13aS)-3-methoxy-12-[3-(8-azaspiro-7,9-dione-[4.5]decan-8-yl]propanesulfonyl-5,6,8a,9,10,11,12,12a,13,13a-decahydro-8H-isoquino[2,1-g][1,6]naphthyridine (8aR,12aS,13aS)-3-methoxy-12-[3-(8-azaspiro-7,9-dione-[4.5]decan-8-yl]propanesulfonyl-5,6,8a,9,10,11,12,12a,13,13a-decahydro-8H-isoquino[2,1-g][1,6]naphthyridine acetate (1.0 g) is dissolved in 50 ml 5N aqueous hydrochloric acid, and the solution evaporated to dryness. The product is suspended in ethyl acetate and filtered, air dried and recrystallized from methanol/acetone to yield (8aR,12aS,13aS)-3-methoxy-12-[3-(8-azaspiro-7,9-dione-[4.5]decan-8-yl]propanesulfonyl5,6-,8a,9,10,11,12,12a,13,13a-decahydro-8H-isoquino-[2,1-g][1,6]naphthyridine hydrochloride.

In a similar manner, substituting for hydrochloric acid other acids, such as sulfuric acid, nitric acid, phosphoric acid and the like, other acid addition salts of all compounds of Formula (I) are prepared.

In Examples 6 through 11 the active ingredient is (8aR,12aS,13aS)-3-methoxy-12-[3-(8-azaspiro-7,9-dione[4.5]decan-8-yl]propanesulfonyl-5,6,8a,9,10,11,12,12a,13,13a-decahydro-8H-isoquino[2,1-g][1,6]naphthyridine hydrochloride. Other compounds of Formula (I) and the pharmaceutically acceptable salts thereof may be substituted therein.

EXAMPLE 6

Composition for Oral Administration

| The composition contains: | % wt./wt. |
| --- | --- |
| Active ingredient | 40% |
| Lactose | 59.5% |
| Magnesium stearate | 0.5% |

The two ingredients are milled, mixed and dispensed into capsules containing 125-250 mg each; one capsule would approximate a total daily dosage of 50-100 mg.

EXAMPLE 7

Composition for Oral Administration

| The composition contains: | % wt./wt. |
| --- | --- |
| Active ingredient | 50.0% |
| Microcrystalline cellulose | 45.0% |
| Croscarmellose sodium | 2.0% |
| PVP (polyvinylpyrrolidine) | 2.0% |
| Magnesium stearate | 1.0% |

The first four ingredients above are combined and granulated using water as solvent. The formulation is then dried, blended with the magnesium stearate, and formed into tablets (containing 50-100 mg of active compound) with an appropriate tableting machine.

EXAMPIE 8

Parenteral Formulation (IV)

| The composition contains: | % wt./wt. |
| --- | --- |
| Active ingredient | 2.00% |
| Propylene glycol | 20.0% |
| Polyethylene glycol 400 | 20.0% |
| Polysorbate 80 | 1.0% |
| 0.9% Saline solution qs ad | 100 ml |

The active ingredient is dissolved in propylene glycol, polyethylene glycol 400 and polysorbate 80. A sufficient quantity of 0.9% saline solution is then added with stirring to provide 100 ml. of the I.V. solution which is filtered through a 0.2 micron membrane filter and packaged under sterile conditions.

EXAMPLE 9

Suppository Formulation

| The composition contains: | % wt./wt. |
| --- | --- |
| Active ingredient | 5.0% |
| Witepsol W | 95.0% |

The ingredients are melted together and mixed on a steam bath, and poured into moulds containing 1-2 g total weight.

EXAMPLE 10

Topical Formulation

| Ingredients | grams |
| --- | --- |
| Active compound | 5-10 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the above ingredients, except water, are combined and heated to 60° C. with stirring. A sufficient quantity of water at 60° C. is then added with vigorous stirring to emulsify the ingredients, and water then added q.s. 100 g.

EXAMPLE 11

Composition for Topical Administration to the Eye

| The composition contains: | % wt/vol |
| --- | --- |
| Active ingredient | 1-2 |
| Benzalkonium chloride | 0.02 |
| EDTA | 0.01 |
| Phenylethanol | 0.25 |
| Boric acid | 1.62 |
| water qs | 100 ml |

The first four ingredients are dissolved in less than the required total volume of water, and the pH adjusted to 7.4. The volume is then brought to 100 ml with additional water.

EXAMPLE 12

Determination of Affinity at $\alpha_2$-adrenoceptors and 5-HT$_{1A}$ receptors

Membrane Preparation

Male Sprague-Dawley rats (150–200g) were killed by cervical dislocation, and the brains rapidly removed and dissected on ice. Cerebral cortices were homogenized in 25 volumes of Tris buffer (50 mM Tris hydrochloride, 5 mM EDTA; pH 7.4 at 25° C.), using a polytron PT 10 (setting 10; two 10-second bursts). The homogenate was then centrifuged at 49,000 g for 15 minutes at 4° C. After a second wash, the pellet obtained was resuspended in Tris assay buffer (50 mM Tris hydrochloride, 5 mM EDTA; pH 7.4 at 25° C.) before undergoing two further washes. The final pellet was resuspended in assay buffer for direct use in binding assays.

$\alpha$-Adrenoceptor Binding Assay

The affinity of the compounds of formula (I) for $\alpha_2$-adrenoceptors was assayed in rat cortex by the method of Brown et al., *Br. J. Pharmacol.*, Vol. 99, pp 803–809 (1990).

Protocol: The above prepared rat cerebral membrane (500 μg protein) was incubated with [$^3$H]-yohimbine (1.5 nM) in the presence or absence of a range of 12 concentrations of the competing ligand in a total volume of 500 μl Tris assay buffer. Non-specific binding was defined as the concentration of bound ligand in the presence of 10 μM phentolamine. Specific binding represented 60–70% of total binding at 1.5 nM [$^3$H]-yohimbine. Following equilibrium (30 minutes at 25° C.), bound radioactivity was separated from free by vacuum filtration, and determined by liquid scintillation spectrometry. Saturation assays were performed under similar conditions using a range of concentrations of [$^3$H]-yohimbine (0.1–15 nM).

The compounds of the present invention showed activity when tested by this procedure.

5-HT$_{1A}$ Receptor Assay

The affinity of the compounds of formula (I) for 5-HT$_{1A}$ receptors was assayed in rat cortex by the method of Kilpatrick et al., *Europ. J. Pharmacol.*, Vol. 166, pp 315–318.

Protocol: The above prepared rat cerebral membrane (300 μg protein) was incubated with [$^3$H]8-hydroxy-DPAT (1.5 nM) in a 50 nM Tris HCl buffer, pH 7.4, containing 5 nM magnesium sulfate and 0.5 nM EDTA. Incubations were carried out for 10 minutes at 37° C. in a final volume of 2.0 ml. Non-specific binding was determined in the presence of 3 μM of Buspirone and represented approximately 20% of specific [$^3$H]8-hydroxy-DPAT binding.

The compounds of the present invention showed activity when tested by this procedure.

EXAMPLE 13

Assay for pre- and post-synaptic $\alpha_2$-adrenoceptor blockade

Protocol:

Ileum preparations were taken from female Dunkin Hartley guinea pigs in the weight range of 250–300 grams, and set up in 30 ml isolated organ baths containing physiological Tyrode solution of the following composition (mmol.L$^{-1}$):

NaCl—136.89, KCl—2.68, MgCl$_2$.6H$_2$O—1.05, NaH$_2$PO$_4$.2H$_2$O—0.42, Glucose—5.55, NaHCO$_3$—11.9, CaCl$_2$.6H$_2$O—1.8

The mixture was gassed with 100% oxygen and maintained at 37° C. An initial tension of 1 gram was applied. The preparations were field stimulated at 0.1 Hz (1 msec pulse durations, supramaximal voltage) via a stainless steel electrode passing through the lumen. The resulting contractions were recorded isometrically on a Lectromed oscillograph. After an equilibrium period of 1 hour an initial cumulative dose-response curve to the agonist UK14304 was obtained. The preparations were then washed thoroughly to remove all of the agonist and left to equilibrate for a further 40 minutes, after which a second cumulative dose-response curve to the agonist was obtained and measured as the control. The preparations were then treated with the antagonists of Formula (I) for 40 minutes, and then concentration-response curves to the agonist determined. The compounds of the present invention showed activity when tested by this procedure.

Alternatively, the procedure according to Caroon, J. M. et al., J. Med. Chem., 1982, Vol. 25, 666, as set forth in U.S. Pat. No. 4,791,108, may be used for determining pre- and post-synaptic $\alpha_2$-adrenoceptor blockade in compounds of Formula (I).

EXAMPLE 14

Determination of Partial Agonist Activity at 5-HT$_{1A}$ Receptors

Partial agonist activity of the compounds of Formula (I) was measured by the method of Small et al., *Br. J. Pharmacol.*, Vol. 98, pp 756 (1989).

Protocol:

Ileum preparations, taken from female Dunkin-Hartley guinea-pigs in the weight range of 250–500 g, were set up in 30 ml isolated organ baths filled with low Ca$^{2+}$ Tyrodes solution (composition: NaCl 137 mM, KCl 2.7 mM, CaCl$_2$ 0.9 mM, MgCl$_2$ 1.1 mM, NaH$_2$PO$_4$ 0.42 mM, NaHCO$_2$ 11.9 mM, glucose 5.5 mM; pH 7.4 at 37° C., gassed with oxygen) and stimulated via two parallel stainless steel electrodes, one of which passed through the lumen, at 0.1 Hz (1 msec pulse duration, supramaximal voltage). The contractions in response to electrical stimulation are inhibited by partial agonists at 5-HT$_{1A}$ receptors.

The agonist dipropyl-5-carboxamidotryptamine and the compounds of the predent invention show activity when tested by this procedure.

EXAMPLE 15

Determination of Platelet Aggregation Inhibition

Protocol:

Blood platelets are collected in the standard manner, and incubated in an Aggregation Module Incubator-Cuvette in the presence of either the inhibitor to be tested, or in the absence of said inhibitor as a control. The aggregation of the platelets is observed after the addition of an inducer, and the samples are evaluated for the presence of a lag period and the slope of the aggregation curve, as well as the maximum height of the aggregation curve in comparison to the control. IC$_{50}$ values i.e. the concentration of inhibitor required for 50% inhibition can be calculated from the inflection point on the appropriate dose response curve. The compounds of the present invention show activity when tested by this procedure.

Determination of Effect on Intraocular Pressure

Protocol

The compound to be tested is dissolved in saline, and applied topically to the eye. The intraocular pressure is measured immediately before application, and at specified time intervals thereafter, by means of a probe which measures the force necessary to flatten a small area of corneal surface, according to the method described by Moses, R. A., *Tr. Am. Acad. Opth. and Otol.*, Jan-Feb 1962: 88–95. The compounds of the present invention show activity when tested by this procedure.

EXAMPLE 17

Determination of Effect on Rat Sexual Behavior

The compounds were tested by a modification of the method described in "Sexual Behaviour in Developing Male Rats", P. Sodersten, D. A Dammassa and E. R. Smith, *Hormones and Behaviour*, Vol. 8, pp 320–334 (1977).

Protocol

Sexually-naive Sprague-Dawley male rats (not exposed to female rats since weaning), weighing 200–250 g, were housed two to a cage in a normal light-cycle room (lights on 5.00 a.m., lights off 7.00 p.m.). The animals were grouped according to their weight after a 10 day acclimatization period, and tested on either the 12th or 13th day. The compound to be tested was administered 30 minutes before evaluating for sexual activity.

Stimulus female Sprague-Dawley rats, housed in a reverse light-cycle room (lights off 10 00 a.m., lights on 8.00 p.m.), were brought into sexual receptivity by injection with 20 μg of estradiol benzoate in 0.1 ml of sesame seed oil 48 hours prior to the test, and with 1 mg of progesterone in 0.1 ml of sesame seed oil 4–6 hours prior to the test.

Each male rat treated with the test compound was placed in an observation cage and allowed to acclimatize for 10 minutes. A stimulus female was then introduced into the cage and the behavior of the male (mounts, intromissions and ejaculations) recorded on an Esterline Angus event recorder. Intromission latency (time from the start of the test to the first intromission), ejaculation latency (time from the first intromission to ejaculation), and post-ejaculatory interval (time from ejaculation to the next following intromission) were also recorded. Tests were terminated if the intromission latency was longer than 15 minutes, the ejaculation latency was longer than 30 minutes, or the post-ejaculatory interval was in excess of 15 minutes.

Enhanced activity was measured by an increase in one or more behavior scores. The compounds of the present invention show activity when tested by this procedure.

EXAMPLE 18

Hypoglycaemic Assay

A compound of Formula (I) was administered to groups of 10 male mice (30 mg/kg, intraperitoneally) and found to reduce blood glucose; these hypoglycaemic effects indicate potential utility as an antidiabetic agent.

EXAMPLE 19

Blood Pressure Lowering Assay

Compounds of Formula (I) will lower blood pressure in normotensive rats anaesthetized with pentobarbitone when administered intravenously. The mean blood pressure is monitored by an indwelling catheter in the carotid artery.

EXAMPLE 20

Selective Vasodilation Assay

Tail Skin Temperature and Core Temperature

Male Sprague-Dawley rats weighing 200–300 grams were housed in pairs at a temperature of 18°–20° C. for 2–6 days before carrying out the assay. One hour before the first measurement the rats were placed in well-ventilated transparent holding cages (length 18 cm, width 12 cm, height 10 cm) and restrained by passing the tail through a 2 cm diameter aperture at the rear of the cage and taping it to a rod which protruded from the rear wall immediately above the opening. A plastic or rubber-covered thermocouple was inserted 5 cm past the anal sphincter and taped to the tail. A flat disc thermocouple (diameter 7 mm) was affixed to the dorsal surface of the tail using two layers of tape. Readings of ambient temperature (Ta), core temperature (Tc), and tail skin temperature (Ts) were taken at 5 minute intervals for 75 minutes. Immediately after the fourth reading the rats were dosed with the drug, by oral intubation or by subcutaneous injection. For each treatment the measurements were compared with those of the appropriate control group. The compounds of Formula (I) evoked an increase in tail skin temperature.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A compound represented by the formula

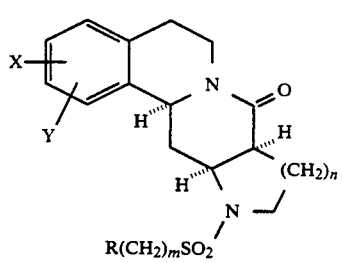

wherein:

m is an integer of 1-6;

n is 1 or 2;

X and Y are independently hydrogen; hydroxy; lower alkyl; lower alkoxy; or halo; or X and Y when adjacent and taken together are methylenedioxy or ethylene-1,2-dioxy;

R is

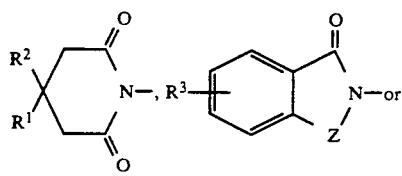

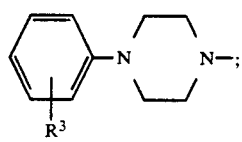

wherein:

R$^1$ and R$^2$ are independently hydrogen or lower alkyl, or when taken together with the carbon to which they are attached are cycloalkyl;

R$^3$ is hydrogen, lower alkyl, lower alkoxy, hydroxy, trifluoromethyl or halo; and

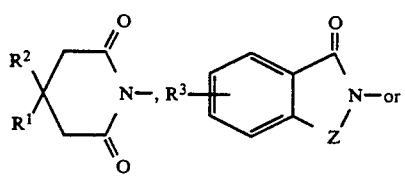

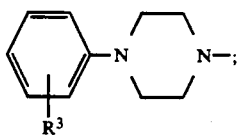

or a pharmaceutically acceptable salt thereof.

2. The compound of claim 1 wherein n is 2, or a pharmaceutically acceptable salt thereof.

3. The compound of claim 2 wherein R is

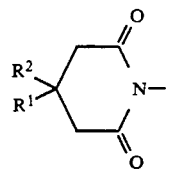

or a pharmaceutically acceptable salt thereof.

4. The compound of claim 3 wherein X and Y are independently hydrogen or lower alkoxy having one to four carbon atoms, or X and Y taken together are methylenedioxy, or a pharmaceutically acceptable salt thereof.

5. The compound of claim 4 wherein R$^1$ and R$^2$ together with the carbon to which they are attached are cyclopentyl, m is 3, X is 3-methoxy and Y is hydrogen, namely (±)-(8aα,12aα,13aα)-3-methoxy-12-[8-(3-propyl)-8-azaspiro[4.5]decan-7,9-dione]sulfonyl-5,6,8a,9,10,11,12,12a,13,13a-decahydro-8H-isoquino[2,1-g][1,6]naphthyridine, or a pharmaceutically acceptable salt thereof.

6. The (8aR,12aS,13aS) isomer of a compound of claim 5, namely (8aR,12aS,13aS)-3-methoxy-12-[8-(3-propyl)-8-azaspiro-[4.5]decan-7,9-dione]sulfonyl-5,6,8a,9,10,11,12,12a,13,13a-decahydro-8H-isoquino[2,1-g][1,6]naphthyridine, or a pharmaceutically acceptable salt thereof.

7. The compound of claim 4 wherein R$^1$ and R$^2$ are both methyl, m is 3, X is 3-methoxy and Y is hydrogen, namely (±)-(8aα,12aα,13aα)-3-methoxy-12-[3-(3,3-dimethylglutarimid-1-yl)propanesulfonyl]-5,6,8a,9,10,11,12,12a,13,13a-decahydro-8H-isoquino[2,1-g][1,6]naphthyridine, or a pharmaceutically acceptable salt thereof.

8. The (8aR,12aS,13aS) isomer of a compound of claim 7, namely (8aR,12aS,13aS)-3-methoxy-12-[3-(3,3-dimethylglutarimid-1-yl)propanesulfonyl]-5,6,8a,9,10,11,12,12a,13,13a-decahydro-8H-isoquino[2,1-g][1,6]naphthyridine, or a pharmaceutically acceptable salt thereof.

9. The compound of claim 2 wherein R is

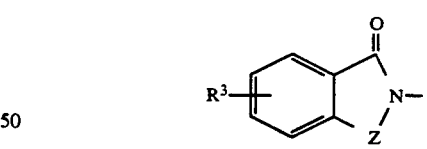

or a pharmaceutically acceptable salt thereof.

10. The compound of claim 9 wherein X and Y are independently hydrogen or lower alkoxy having one to four carbon atoms, or X and Y taken together are methylenedioxy, or a pharmaceutically acceptable salt thereof.

11. The compound of claim 10 wherein m is 3, R$^3$ is hydrogen and Z is —SO$_2$, or a pharmaceutically acceptable salt thereof.

12. The compound of claim 11 wherein X is 3-methoxy and Y is hydrogen, namely (±)-(8aα,12aα,13aα)-3-methoxy-12-{3-[2-(benzoisothiazole-3(2H)-one-1,1-dioxide)]-propanesulfonyl}-5,6,8a,9,10,11,12,12a,13,13a-decahydro-8H-isoquino[2,1-g][1,6]naphthyridine, or a pharmaceutically acceptable salt thereof.

13. The (8aR,12aS,13aS) isomer of claim 12, namely (8aR,12aS,13aS)-3-methoxy-12-{3-[2-(benzoisothiazole-3(2H)-one-1,1-dioxide)]propanesulfonyl}-5,6,8a,9,10,11,12,12a,13,13a-decahydro-8H-isoquino[2,1-g][1,6]naphthyridine, or a pharmaceutically acceptable salt thereof.

14. The compound of claim 2 wherein R is

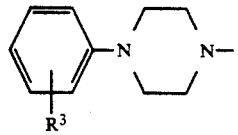

or a pharmaceutically acceptable salt thereof.

15. The compound of claim 14 wherein X and Y are independently hydrogen or lower alkoxy having one to four carbon atoms, or X and Y taken together are methylenedioxy, or a pharmaceutically acceptable salt thereof.

16. The compound of claim 15 wherein m is 3 and $R^3$ is lower alkoxy, or a pharmaceutically acceptable salt thereof.

17. The compound of claim 16 wherein $R^3$ is 2--methoxy, X is 3-methoxy and Y is hydrogen, namely ($\pm$)-(8a$\alpha$,12a$\alpha$,13a$\alpha$)-3-methoxy-12-{3-[4-(2-methoxyphenyl)piperazin-1-yl]propanesulfonyl}-5,6,8a,9,10,11,12,12a,13,13a-decahydro-8H-isoquino[2,1-g][1,6]-naphthyridine, or a pharmaceutically acceptable salt.

18. The (8aR,12aS,13aS) isomer of a compound of claim 17, namely (8aR,12aS,13aS)-3-methoxy-12-{3-[4-(2-methoxyphenyl)piperazin-1-yl]propanesulfonyl}-5,6,8a,9,10,11,12,12a,13,13a-decahydro-8H-isoquino[2,1-g][1,6]-naphthyridine, or a pharmaceutically acceptable salt thereof.

19. The compound of claim 1 wherein n is 1, or a pharmaceutically acceptable salt thereof.

20. The compound of claim 19 wherein R is

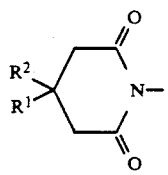

or a pharmaceutically acceptable salt thereof.

21. The compound of claim 20 wherein m is 3, and X and Y are independently hydrogen or lower alkoxy having one to four carbon atoms, or X and Y taken together are methylenedioxy, or a pharmaceutically acceptable salt thereof.

22. The compound of claim 19 wherein R is

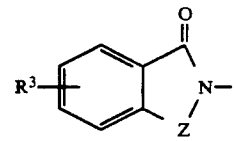

or a pharmaceutically acceptable salt thereof.

23. The compound of claim 22 wherein m is 3, and X and Y are independently hydrogen or lower alkoxy having one to four carbon atoms, or X and Y taken together are methylenedioxy, or a pharmaceutically acceptable salt thereof.

24. The compound of claim 19 wherein R is

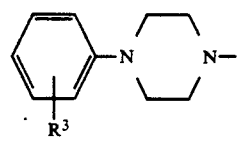

or a pharmaceutically acceptable salt thereof.

25. The compound of claim 24 wherein m is 3, $R^3$ is lower alkoxy, and X and Y are independently hydrogen or lower alkoxy having one to four carbon atoms, or X and Y taken together are methylenedioxy, or a pharmaceutically acceptable salt thereof.

26. A pharmaceutical composition comprising a therapeutically effective amount of a compound of claim 1, or a pharmaceutically acceptable salt thereof, in admixture with one or more pharmaceutically acceptable non-toxic carriers.

27. A method for treating a mammal having a disease state which is alleviable by treatment with an $\alpha_2$-adrenoceptor antagonist or a 5-HT$_{1A}$ receptor partial agonist, which method comprises administering to a mammal in need thereof a therapeutically effective amount of a compound of claim 1, or a pharmaceutically acceptable salt thereof.

28. The method of claim 27, wherein the disease state is selected from the group consisting of sexual dysfunction, depression and anxiety.

* * * * *

UNITED STATES PATENT AND TRADEMARK OFFICE
CERTIFICATE OF CORRECTION

PATENT NO. : 5,229,387

DATED : July 20, 1993

INVENTOR(S) : Clark, et al.

It is certified that error appears in the above-identified patent and that said Letters Patent is hereby corrected as shown below:

Claim 1, at column 55, line 12: "$R(CH_2)_mSO_2$" should read --$R(CH_2)_mO_2S$--

Claim 1, at column 55, lines 46-64: "trifluoromethyl or halo; and

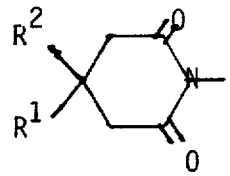 , 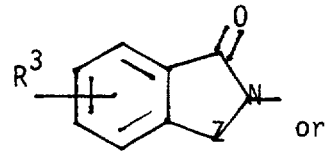 or 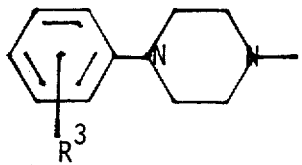

or a pharmaceutically acceptable salt thereof."

should read --trifluoromethyl or halo; and

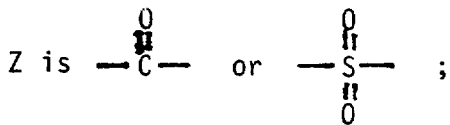

or a pharmaceutically acceptable salt thereof.--

Claim 17, at column 57, lines 25-26: "The compound of claim 16 wherein $R^3$ is 2-- -methoxy," should read --The compound of claim 16 wherein $R^3$ is 2-methoxy,--

Claim 17, at column 57, lines 30-31: "or a pharmaceutically acceptable salt." should be --or a pharmaceutically acceptable salt thereof.--

UNITED STATES PATENT AND TRADEMARK OFFICE
CERTIFICATE OF CORRECTION

PATENT NO. : 5,229,387

DATED : July 20, 1993

INVENTOR(S) : Robin D. Clark, et al.

It is certified that error appears in the above-identified patent and that said Letters Patent is hereby corrected as shown below:

Claim 18, at column 57, lines 32-33: "The (8aR,12aS,13aS) isomer of a compound of claim 17," should be --The (8aR,12aS,13aS) isomer of claim 17,--

Signed and Sealed this

Thirtieth Day of November, 1993

BRUCE LEHMAN

*Attest:*

*Attesting Officer*    *Commissioner of Patents and Trademarks*

UNITED STATES PATENT AND TRADEMARK OFFICE
CERTIFICATE OF CORRECTION

PATENT NO. : 5,229,387
DATED : July 20, 1993
INVENTOR(S) : Clark et al.

It is certified that error appears in the above-identified patent and that said Letters Patent is hereby corrected as shown below:

Claim 1, at column 55, line 5: the double bond attached to the oxygen should not be present.

Signed and Sealed this

Fourteenth Day of June, 1994

*Attest:*

BRUCE LEHMAN

*Attesting Officer*    *Commissioner of Patents and Trademarks*